(12) United States Patent
Johnson

(10) Patent No.: US 7,429,477 B2
(45) Date of Patent: *Sep. 30, 2008

(54) CONTROLLING PLANT PATHOGENS WITH BACTERIAL/FUNGAL ANTAGONIST COMBINATIONS

(76) Inventor: Thomas D. Johnson, P.O. Box 12, Buffalo, SD (US) 57720

( * ) Notice: Subject to any disclaimer, the term of this patent is extended or adjusted under 35 U.S.C. 154(b) by 335 days.

This patent is subject to a terminal disclaimer.

(21) Appl. No.: 10/940,036

(22) Filed: Sep. 13, 2004

(65) Prior Publication Data

US 2005/0096225 A1    May 5, 2005

Related U.S. Application Data

(63) Continuation-in-part of application No. 10/067,185, filed on Feb. 1, 2002, now Pat. No. 6,808,917.

(60) Provisional application No. 60/265,998, filed on Feb. 2, 2001.

(51) Int. Cl.
*C12N 1/20* (2006.01)
*C12N 1/14* (2006.01)
*C12N 1/00* (2006.01)
*A01N 63/00* (2006.01)
*A01N 63/04* (2006.01)

(52) U.S. Cl. .............. 435/252.4; 435/252.5; 435/256.7; 435/839; 435/945; 424/93.3; 504/117

(58) Field of Classification Search .................. 504/117; 435/252.4

See application file for complete search history.

(56) References Cited

U.S. PATENT DOCUMENTS 6,309,440 B1 * 10/2001 Yamashita ...................... 71/27
6,699,707 B1 *  3/2004 Hince ......................... 435/262
6,808,917 B1 * 10/2004 Johnson .................... 435/252.4

OTHER PUBLICATIONS

Mao et al. "Biocontrol of selected soilborne diseases of tomato and pepper plants". Crop Protection. Aug. 1998, vol. 17, No. 6, pp. 535-542.*
Amal de Silva et al. "Growth promotion of highbush blueberry by fungal and bacterial inoculants". Hortscience. Dec. 2000, vol. 35, No. 7, pp. 1228-1230.*
Krebs et al. "Use of *Bacillus subtilis* as biocontrol agent". Zeitschrift fuer pflanzenkrankheiten und Pflanzenschutz. Mar. 1998, vol. 105, No. 2, pp. 181-197.*
Abuzinadah, R., Finay, R., and Read, D. The role of proteins in nitrogen nutrition of ectomycorrhizal plants. II. Utilization of peptides and proteins by ectomycorrhizal plants of *Pinus contorta*. New Phytologist. 1986, pp. 495-506, vol. 103.
Altomare, C., Norvell, W., Bjorkman, T., and Harman, G. Solubilization of Phosphates and Micronutrients by the Plant-Growth-Promoting and Biocontrol Fungus *Trichoderma harzianum* Rifai 1295-22.

Applied and Environmental Microbiology, 1999, pp. 2926-2933, vol. 65, No. 7.
Anusuya, D. and Jayarajan, R. Solubilization of phosphorus by *Trichoderma viride*. Current Science, 1998, pp. 464-466, vol. 74, No. 5.
Chapin III, F., Moilanen, L., and Kielland, K. Preferential use of organic nitrogen for growth by a non-mycorrhizal artic sedge. Nature, 1993, pp. 150-152, vol. 361.
Cunningham J., E. and Kuiack, C. Production of citric and oxalic acids and solubilization of calcium phosphate by *Penicillium bilaii*. Applied and Environmental Microbiology, 1992, pp. 1451-1458, vol. 58.
Finlay, R., Frostegard, A. and Sonnerfeldt, A. Utilization of organic and inorganic nitrogen sources by ectomycorrhizal fungi in pure culture and in symbiosis with *Pinus contorta* Dougl. Ex. Loud. New Phytologist, 1992, pp. 105-115, vol. 120.
Gomes, J., Gomes, I., Esterbauer, H., Kreiner, W. and Steiner, W. Production of cellulases by a wild strain of *Gliocladium virens*: optimization of the fermentation medium and partial characterization of the enzymes. Applied Microbiology and Biotechnology, 1989. pp. 601-608, vol. 31, Nos. 5-6.
Harman, G., Howell, C., Viterbo, A., Chet, I., and Lorito, M. *Trichoderma* species—opportunistic avirulent plant symbionts. Nature Reviews: Microbiology. 2004, pp. 43-56, vol. 2, No. 1.
Holker, U., Schmiers, H., Grosse, S., Winkelhofer, M., Polsakiewicz, M., Ludwig, S., Dohse, J., and Hofer, M. Solubilization of low rank coal by *Trichoderma atroviride*: Evidence for the involvement of hydrolytic and oxidative enzymes using 14C-labelled lignite. Journal of Industrial Microbiology & Biotechnology, 2002, pp. 207-212, vol. 28.
Howell, C., and Stipanovic, R. Mechanisms in the Biocontrol of Rhizoctonia solani-Induced Cotton Seedling Disease by *Gliocladium virens*: Antibiosis. Phytopathology, 1995, pp. 469-472.
Johnsson, L., Berggren, D., and Karen, O. Content and bioavailability of organic forms of nitrogen in the O horizon of a podzol. European Journal of Soil Science, 1999, pp. 591-600, vol. 50.
Laborda, F., Monistrol, F., Luna, N., and Fernandez, M. Process of liquefaction/solubilization of Spanish coals by microorganisms. Applied Microbiology and Biotechnology, 1999, pp. 49-56, vol. 52. No. 1.
Lindahl, B., Taylor, A. and Finay, R. Defining nutritional constraints on carbon cycling in boreal forests—towards less a 'phytocentric' perspective. Pland and Soil, 2002, pp. 123-135, vol. 242.
Sawyer, S., Chambers, and Cairney J. Variation in nitrogen source utilization by nine *Amanita muscaria* genotypes from Australian Pinus radiate plantations. Mycorrhiza, 2003, pp. 217-221, vol. 13.

(Continued)

*Primary Examiner*—Vera Afremova
(74) *Attorney, Agent, or Firm*—Robert M Hunter

(57) ABSTRACT

Fungal/bacterial antagonist combinations, a seed coated with one of the combinations and a plant protected from plant pathogens by one of the combinations. The invention is also a fungal/bacterial antagonist combination comprising a *Trichoderma virens* fungal antagonist and a *Bacillus subtilis* var. *amyloliquefaciens* (*Bacillus amyloliquefaciens*) bacterial antagonist and its use for controlling plant pathogens as a biocontrol agent, bio-pesticide or bio-fungicide. The invention also finds utility as a fungal/bacterial antagonist combination applied to the seed, stalk or leaf that results in an increase in plant yield. Control of early and late season stalk and root rot caused by fungi such as Fusarium, Phythium, Phytophthora and Penicillium in tomatoes, peppers, turf grass, soybeans, sunflower, wheat and corn is achieved.

5 Claims, 2 Drawing Sheets

OTHER PUBLICATIONS

Figure 1:
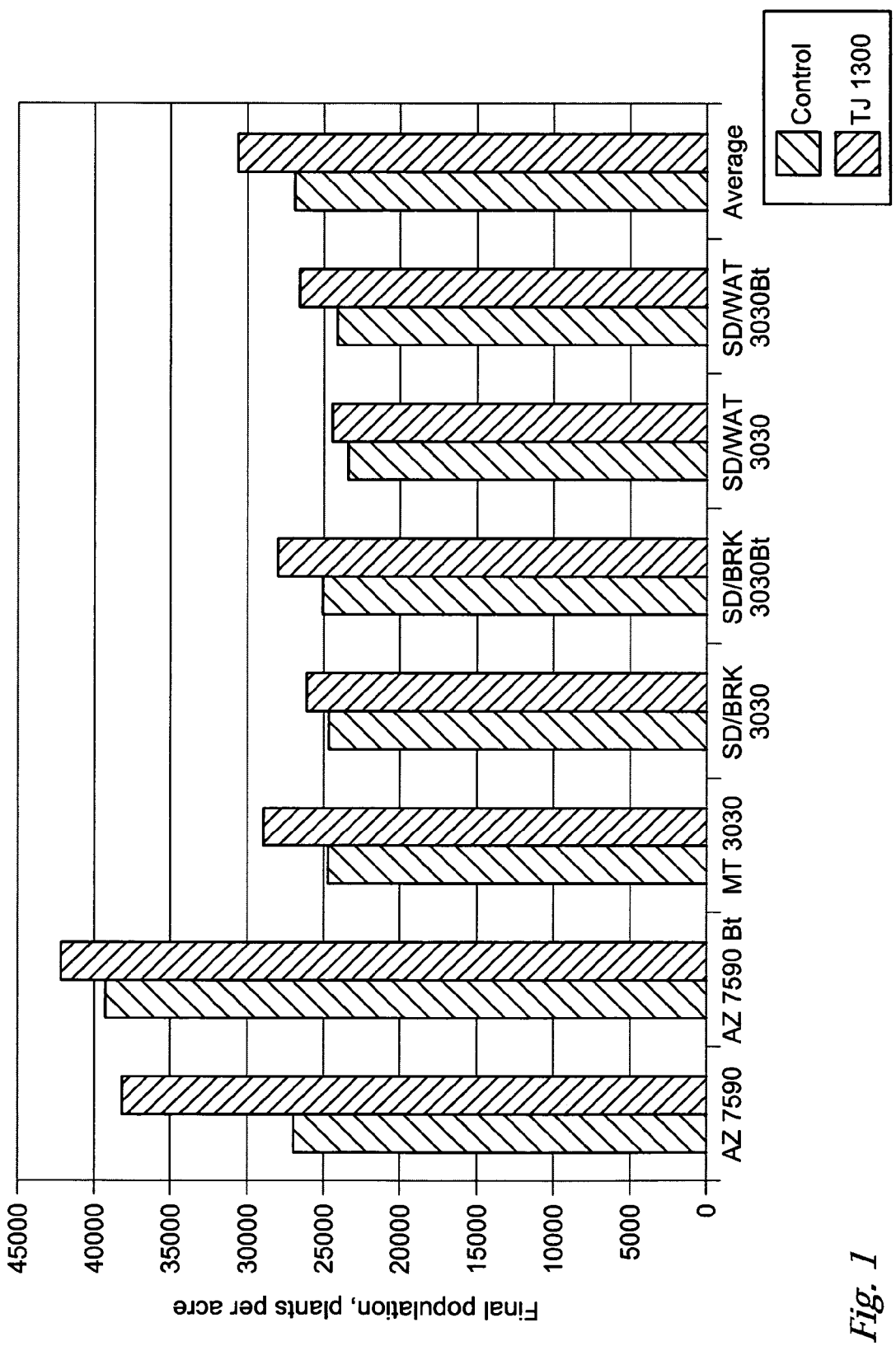

Schulten, R. and Schnitzer, M. The chemistry of soil organic nitrogen: a review. Biology & Fertility of Soils, 1998, pp. 1-15, vol. 26.

Srinath, J., Bagyaraj, D., and Satyanarayana, B. Enhanced growth and nutrition of micropropagated *Ficus benjamina* to *Glomus mosseae* co-inoculated with *Trichoderma harzianum* and *Bacillus coagulans*. World Journal of Microbiology & Biotechnology, 2003, pp. 69-72, vol. 19.

Turnbull, M., Schmidt, S., Erskine, P., Richards, S. and Stewart, G. Root adaptation and nitrogen source acquisition in natural ecosystems. Tree Physiology, 1996, pp. 941-948, vol. 16.

Whitney, D. Phosphorus Facts. Kansas State Cooperative Extension Service. C-665 Revised. File Code: Crops & Soils 4-1, Oct. 1998.

Wu, T., Kabir, Z., and Koide R. A possible role for saprotrophic microfungi in the N nutrition of ectomycorrhizal *Pinus resinosa*. Soil Biology and Biochemistry, 2004, pp. 965-975, vol. 37, Issue 5.

Greiner, R., and Larsson Alminger, M. Stereospecifcity of myo-inositol hexakisphosphate dephosphorylation by phytate-degrading enzymes of cereals. Journal of Food Biochemistry, 2001, pp. 229-248, vol. 25.

Hayes, J. E., Simpson, R. J. and Richardson, A. E. The growth and phosphorus utilization of plants in sterile media when supplied with inositol hexaphosphate, glucose-1-phosphate or inorganic phosphate. Plant and Soil, 2000, pp. 165-174, vol. 220.

Idriss, E., Makarewicz, O., Farouk, A., Rosner, K., Greiner, R., Bochow, H., Richter, T., and Borriss, R. Extracellular phytase activity of *Bacillus amyloliquefaciens* FZB45 contributes to its plant-growth-promoting effect. Microbiology, 2002, pp. 2097-2109, vol. 148.

Igbasan, F. A., Manner, K., Miksch, G., Borriss, R., Farouk, A., and Simon, O. Comparative studies of the in vitro properties of phytases from various microbial origin. Archives of Animal Nutrition, 2000, pp. 353-373, vol. 53.

Jiang, G., Krishnan, A., Kim, Y., Wacek, T. and Krishnan, H. A functional myo-inositol dehydrogenase gene is required for efficient nitrogen fixation and competitiveness of *Sinorhizobium fredii* USDA191 to nodulate soybean (Glycine max [L.] Merr.). Journal of Bacteriology, 2001, pp. 2595-2604, vol. 183.

Kerovuo, J. A Novel Phytase from *Bacillus*. Characterization and Production of the Enzyme. Academic Dissertation, 2000, University of Helsinki, Finland.

Kim, Y. O., Lee, J. K., Kim, H. K., Yu, J. H. and Oh, T. K. Cloning of the thermostable phytase (Phy) from *Bacillus* sp. DS11 and its overexpression in *Escherichia coli*. FEMS Microbiology Letters, 1998, pp. 185-191, vol. 162.

Kim, D. H., Oh, B. C., Choi, W. C., Lee, J. K., and Oh, T. K. Enzymatic evaluation of *Bacillus amyloliquefaciens* phytase as a feed additive. Biotechnology Letters, 1999a, pp. 925-927, vol. 21.

Kim, Y. O., Lee, J. K., Oh, B. C., and Oh, T. K. High-level expression of a recombinant thermostable phytase in *Bacillus subtilis*. Bioscience Biotechnology and Biochemestry, 1999b, pp. 2205-2207, vol. 63.

Powar, V. K., and Jagannathan, V. Purification and properties of phytate-specific phosphatase from *Bacillus subtilis*. Journal of Bacteriology, 1982, pp. 1102-1108, vol. 151.

Richardson, A., E., Hadobas, P., A. and Hayes, J. E. Acid phosphomonesterase and phytase activity of wheat (*Triticum aestivum* L.) roots and utilization of organic phosphorus substrates by seedlings grown in sterile culture. Plant Cell Environment, 2000, pp. 397-405, vol. 23.

Richardson, A. E., Hadobas, P. A. and Hayes, J. E. Extracellular secretion of *Aspergillus* phytase from *Arabidopsis* roots enables plants to obtain phosphorus from phytate. The Plant Journal, 2001a, pp. 641-649, vol. 25.

Richardson, A. E., Hadobas, P. A., Hayes, J. E., O'Hara, J. E., and Simpson, R. J. Utilization of phosphorus by pasture plants supplied with myo-1-inositol hexaphosphate is enhanced by the presence of soil microorganisms. Plant and Soil, 2001b, pp. 47-56, vol. 229.

Shieh, T. R., and Ware, J. H. Survey of Microorganisms for the Production of Extracellular Phytase. Applied Microbiology, 1968, pp. 1348-1351, vol. 16.

Shimizu, M. Purification and characterization of phytase from *Bacillus subtilis* (natto) N-77. Bioscience, Biotechnology and Biochemistry, 1992, pp. 1266-1296, vol. 56.

Yoshida, K. L., Yamamoto, Y., Omae, K., Yamamoto, M., and Fujita, Y. Identification of two myo-inositol transporter genes of *Bacillus subtilis*. Journal of Bacteriology, 2002, pp. 983-991, vol. 184.

Zang, M., Zhou, M., Van Etten, R., Stauffacher, C. Crystal Structure of Bovine Low Molecular Weight Phosphotyrosyl Phosphatase Complexed with the Transition State Analog Vanadate. Biochemistry, 1997, pp. 15-23, vol. 36.

Koide, R. and Kabir, Z. Nutrient economy of red alpine is affected by interactions between *Pisolithus tinctorius* and other forest floor microbes. New Phytologist, 2001, pp. 179-188, vol. 150.

\* cited by examiner

CONTROLLING PLANT PATHOGENS WITH BACTERIAL/FUNGAL ANTAGONIST COMBINATIONS

CROSS-REFERENCE TO RELATED APPLICATIONS

This application is a continuation-in-part of prior U.S. patent application Ser. No. 10/067,185, filed Feb. 1, 2002, now U.S. Pat. No. 6,808,917, which claims the benefit of U.S. Provisional Application No. 60/265,998, filed Feb. 2, 2001; the disclosures of which applications are incorporated by reference as if fully set forth herein.

STATEMENT REGARDING FEDERALLY SPONSORED RESEARCH OR DEVELOPMENT

The U.S. Government has a paid-up license in this invention and the right in limited circumstances to require the patent owner to license others on reasonable terms as provided for by the terms of Grant No. DMI-9901629 awarded by the National Science Foundation.

BACKGROUND OF THE INVENTION

This invention relates to fungal/bacterial antagonist combinations, a seed coated with said combinations and a plant protected from plant pathogens by said combinations. In particular, the invention relates to fungal/bacterial antagonist combinations and their use for controlling plant pathogens.

Early and late season stalk and root rot are major causes of crop loss. A variety of plants are affected, including tomatoes, peppers, turf grass, soybeans, sunflower, wheat and corn. The pathogens that cause these symptoms include fungi of the genera *Fusarium, Phythium, Phytophthora* and *Penicillium*.

One approach to solving the problem of early season damping off of plants is treatment of seeds with fungicides, such as captan, metalaxyl and Maxim. Although these chemicals enhance seed germination and seedling stand by inhibiting the pathogenic ability of *Phythium* spp. (active in cool, wet soils), they have no activity against the pathogenic fungi that are responsible for late season root and stalk rot.

*Fusarium* and *Penicillium* are the pathogens responsible for late season root and stalk rot. These pathogens prefer the warm, dry conditions that occur late in the growing season. There is no chemical or biological fungicide available that addresses the problem of late season root and stalk rot in corn. Currently, the only way to deal with this problem is to periodically rotate to a non-susceptible crop to reduce pathogen numbers. Corn growers can also select hybrids that have better "standability," but such hybrids usually have lower yields. Unfortunately, the corn varieties with the highest yields are usually those most susceptible to late season root and stalk rot.

*Trichoderma* is a genus of fungi that contains about 20 species. Synonyms for the genus name include Aleurisma and Sporoderma. *Trichoderma virens*, which is also called *Gliocladium virens*, is a member of the genus. The natural habitats of these fungi include soil and plant material. A member of the genus, *Trichoderma harzianum* KRL-AG2 (ATCC 20847) also known as strain T-22, is used as a biocontrol agent that is applied as a seed or soil treatment or on cuttings and transplants. Strains of the species, *Trichoderma virens*, have also been used for control of damping off diseases in plants. For example, *Trichoderma (Gliocladium) virens* G1-21 is known and commercially available at a reasonable price, and is being marketed under the trademark SoilGuard® 12G (EPA Registration Number: 70051-3 and EPA Establishment Number: 067250-IL-001). It is manufactured by Thermo Trilogy Corporation of Columbia, Md. Other known and commercially available *Trichoderma virens* strains include those having the following ATCC accession numbers: 10043, 10044, 10045, 13213, 13362, 204067, 204443, 204444, 204445, 20903, 20904, 20906, 24290, 42955, 44327, 44734, 48179, 52045, 52199, 58676, 58677, 58678, 62399, 64271, 74180, 9645, MYA-297, MYA-298, MYA-649 and MYA-650.

*Bacillus* is a genus of rod-shaped, gram-positive, aerobic or (under some conditions) anaerobic bacteria. *Bacillus* species are widely found in soil and water and some have been used to control plant diseases, including root rot. *Bacillus amyloliquefaciens* is a spore-forming member of the genus. *Bacillus amyloliquefaciens* L.L. Campbell strain F (ATCC 23350) is the type strain for the species. Other known and commercially available *Bacillus amyloliquefaciens* strains include those having the following ATCC accession numbers: 23842, 23843, 23844, 23845, 31592, 49763, 53495 and BAA-390 (Int. J. Sys. Bacteriol. 37:69-71, 1987; J. Bacteriol. 94:1124-1130, 1967).

*Bacillus amyloliquefaciens* is also called *Bacillus subtilis* var. *amyloliquefaciens* by some investigators. A protease produced from *Bacillus subtilis* var. *amyloliquefaciens* is commonly used as a tenderized for raw meat products. According to the U.S. Environmental Protection Agency (EPA), *Bacillus subtilis* var. *amyloliquefaciens* strain FZB24 is a naturally-occurring microorganism and widespread in the environment. *Bacillus subtilis* var. *amyloliquefaciens* FZB24 (EPA Registration Number: 72098-5 and EPA Establishment Number: 73386-DEU-001) is known and commercially available at a reasonable price, being marketed under the trademark Taegro® by Earth Bioscience, Inc. of Fairfield, Conn.

*Bacillus lentimorbus* is another spore-forming member of the genus. *Bacillus lentimorbus* Dutky 1940 (ATCC 14707) is the type strain for the species (Skerman, V. B. D., McGowan, V., and Sneath, P. H. A., Approved lists of bacterial names. *Int. J. Syst. Bacteriol.* 30: 225-420, 1980). Some researchers consider *Bacillus lentimorbus* to be a variety of *Bacillus popilliae*. *Bacillus lentimorbus* and *Bacillus popilliae* have recently been reclassified as *Paenibacillus lentimorbus* and *Paenibacillus popilliae* (Pettersson, B., Rippere, K. E., Yousten, A. A. and Priest, F. G., Transfer of *Bacillus lentimorbus* and *Bacillus popilliae* to the genus *Paenibacillus* with emended descriptions of *Paenibacillus lentimorbus* comb. nov. and *Paenibacillus popilliae* comb. nov., *Int. J. Syst. Bacteriol.* 49: 531-540, 1999). *Bacillus lentimorbus* and *Bacillus popilliae* are the causative agents of milky disease in Japanese beetles and related scarab larvae and "milky spore" powders are sold under the trade names, "Doom," "Milky Spore," "Japidemic" "Grub Killer" and "Grub Attack," for biocontrol of these insects.

Background art biocontrol products have comprised the bacterium *Burkholderia cepacia*, which is also known as *Pseudomonas cepacia*. This bacterium has been implicated as a human pathogen. Furthermore, it has little or no shelf life unless refrigerated at 4 degrees Centigrade at a minimum of 20 percent moisture.

The background art is characterized by U.S. Pat. Nos. 4,476,881; 4,489,161; 4,642,131; 4,668,512; 4,678,669; 4,713,342; 4,724,147; 4,748,021; 4,818,530; 4,828,600; 4,877,738; 4,915,944; 4,952,229; 5,047,239; 5,049,379; 5,071,462; 5,068,105; 5,084,272; 5,194,258; 5,238,690; 5,260,213; 5,266,316; 5,273,749; 5,300,127; 5,344,647; 5,401,655; 5,422,107; 5,455,028; 5,409,509; 5,552,138; 5,589,381; 5,614,188; 5,628,144; 5,632,987; 5,645,831; 5,665,354; 5,667,779; 5,695,982; 5,702,701; 5,753,222;

5,852,054; 5,869,042; 5,882,641; 5,882,915; 5,906,818; 5,916,029; 5,919,447; 5,922,603; 5,972,689; 5,974,734; 5,994,117; 5,998,196; 6,015,553; 6,017,525; 6,030,610; 6,033,659; 6,060,051; and 6,103,228.

Gravely et al. in U.S. Pat. No. 4,476,881 disclose a mixed complementary culture of bacteria and fungi that is used to degrade pectin and cellulose components of tobacco materials. The invention is limited in that it teaches use of different microorganisms for a different purpose.

Papavizas in U.S. Pat. No. 4,489,161 discloses a strain of the fungus *Trichoderma viride* that is an effective biocontrol agent for *Fusarium* wilt of chrysanthemum. The invention is limited in that it teaches use of a different microorganism.

Hoitinik in U.S. Pat. No. 4,642,131 discloses a process for production of a disease-suppressive compost and a microorganism culture for use therein. The invention is limited in that it teaches use of different microorganisms for a different purpose.

Lewis et al. in U.S. Pat. No. 4,668,512 disclose a method for preparing pellets containing living biocontrol fungi and nutrients. The invention is limited in that it teaches a process that involves use of different microorganisms.

Ricard in U.S. Pat. No. 4,678,669 discloses a method of using immunizing commensals to control soil-borne pathogens. The invention is limited in that it teaches use of different microorganisms.

Chet et al. in U.S. Pat. No. 4,713,342 disclose a novel isolate of *Trichoderma* and it use. The invention is limited in that it teaches use of a different microorganism.

Marois et al in U.S. Pat. No. 4,724,147 disclose a method for preparing pellets containing living biocontrol fungi. The invention is limited in that it teaches a process that involves use of different microorganisms.

Chet et al. in U.S. Pat. No. 4,748,021 disclose antifungal compositions containing *Trichoderma* active against *Fusarium*. The invention is limited in that it teaches use of a different microorganism.

Marois et al. in U.S. Pat. No. 4,818,530 disclose a method for preparing pellets containing living biocontrol fungi. The invention is limited in that it teaches a process that involves use of different microorganisms.

McCabe et al. in U.S. Pat. No. 4,828,600 disclose a biological inoculant for corn. The invention is limited in that it teaches use of different microorganisms.

Handelsman et al. in U.S. Pat. No. 4,877,738 disclose a new microorganism culture and a method for biological control of damping off and root rot. The invention is limited in that it teaches a process that involves use of a different microorganism, *Bacillus cereus*.

Chet et al. in U.S. Pat. No. 4,915,944 disclose a novel isolate of *Trichoderma* and fungicidal compositions containing it. The invention is limited in that it teaches use of a different microorganism.

Muir in U.S. Pat. No. 4,952,229 discloses a soil and foliar supplement. The invention is limited in that it teaches use of different microorganisms.

Pusey in U.S. Pat. No. 5,047,239 discloses a biological control agent for fruit rot. The invention is limited in that it teaches use of a different microorganism for a different purpose.

Handelsman et al. in U.S. Pat. No. 5,049,379 disclose a fungicidal toxin and a method and an inoculum for controlling root rot and damping off. The invention is limited in that it teaches use of a different microorganism, *Bacillus cereus*.

Kimura in U.S. Pat. No. 5,071,462 discloses a method and apparatus for producing an organic fertilizer. The invention is limited in that it teaches use of different microorganisms for a different purpose.

Lewis et al. in U.S. Pat. No. 5,068,105 disclose a fungal formulation for biocontrol of soil-borne plant pathogens. The invention is limited in that it teaches use of different microorganisms.

Speakman et al. in U.S. Pat. No. 5,084,272 disclose a *Trichoderma* fungus and a fungicide that contains it. The invention is limited in that it teaches use of a different microorganism.

Pauu et al. in U.S. Pat. No. 5,194,258 disclose a method for producing enhanced biocontrol agents. The invention is limited in that it teaches use of different microorganisms.

Elad et al. in U.S. Pat. No. 5,238,690 disclose a novel *Trichoderma* culture and biological compositions containing it. The invention is limited in that it teaches use of different microorganisms for a different purpose.

Harman et al. in U.S. Pat. No. 5,260,213 disclose fused biocontrol agents. The invention is limited in that it teaches use of different microorganisms.

Elad et al. in U.S. Pat. No. 5,266,316 disclose a novel isolate of *Trichoderma harzianum* and fungicidal compositions containing it. The invention is limited in that it teaches use of different microorganisms for a different purpose.

Bok et al. in U.S. Pat. No. 5,273,749 disclose a process for preparing coated microbial pesticides and the products of the process. The invention is limited in that it teaches use of different microorganisms.

Williams in U.S. Pat. No. 5,300,127 discloses seed coatings. The invention is limited in that it teaches use of different microorganisms.

Rossall in U.S. Pat. No. 5,344,647 discloses a *Bacillus* strain that has antimicrobial activity. The invention is limited in that it teaches use of different microorganisms.

Kijima et al. in U.S. Pat. No. 5,401,655 disclose a process for biologically preventing plant diseases. The invention is limited in that it teaches use of different microorganisms for a different purpose.

Kubota in U.S. Pat. No. 5,422,107 discloses a novel fungus and a fungicide containing it. The invention is limited in that it teaches use of a different microorganism.

O'Donnell in U.S. Pat. No. 5,455,028 discloses a method of inhibiting fungi. The invention is limited in that it teaches use of a different microorganism.

Burth et al. in U.S. Pat. No. 5,409,509 disclose a seed treatment. The invention is limited in that it teaches use of different microorganisms.

Shanmuganathan in U.S. Pat. No. 5,525,132 discloses "compositions for the treatment/prevention of microbial diseases of fruit comprising as effective amount of at least one yeast strain . . . " (Abstract). In Example 2, strains are tested separately and are not combined. The disclosed strain D9 was effective and *Trichoderma viridie* was not. Neither was *Bacillus subtilis* effective. The reference teaches that "it is very unpredictable whether a particular yeast species would be effective in the treatment/prevention of microbial disease in fruit" (col. 2, lines 26-28).

Handelsman et al. in U.S. Pat. No. 5,552,138 disclose a novel strain of *Bacillus* cerus and a method of protecting plants with the strain. The invention is limited in that it teaches use of a different microorganism.

Neyra et al. in U.S. Pat. No. 5,589,381 disclose a novel strain of *Bacillus licheniformis* that produces an antifungal agent and a use for the strain. The invention is limited in that it teaches use of a different microorganism.

Urano et al. in U.S. Pat. No. 5,614,188 disclose an anti-*Fusarium* composition containing strains of *Bacillus* sp. The invention is limited in that it teaches use of different microorganisms.

Eastin in U.S. Pat. No. 5,628,144 discloses solid matrix priming of seeds. The invention is limited in that it teaches use of different microorganisms.

Payne et al. in U.S. Pat. No. 5,632,987 disclose a *Bacillus thuringiensis* toxin that is active against corn rootworm larvae. The invention is limited in that it teaches use of a different microorganism for a different purpose.

Chilcott et al. in U.S. Pat. No. 5,645,831 disclose a *Bacillus thuringiensis* strain and metabolite that are active against corn rootworm. The invention is limited in that it teaches use of a different microorganism for a different purpose.

Neyra et al. in U.S. Pat. No. 5,665,354 disclose a novel strain of *Bacillus licheniformis* that produces an antifungal agent and a use for the strain. The invention is limited in that it teaches use of a different microorganism.

Kubo in U.S. Pat. No. 5,667,779 discloses a fungi-inhibiting composition comprising *Bacillus subtilis*. The invention is limited in that it teaches use of a different microorganism.

Handelsman et al. in U.S. Pat. No. 5,695,982 discloses canavanine-resistant strains of *Bacillus cereus*. The invention is limited in that it teaches use of different microorganisms.

Neyra et al. in U.S. Pat. No. 5,697,186 disclose "flocculated bacterial cells" for use "as high-density crop inoculants" (Abstract). The reference is limited to the flocculation of one or more species of bacteria. Combination of bacteria with another type of microorganism is not taught by the reference. Nor, does it teach the combination of more than one bacterium will produce a greater response, only that the flocculation will allow the application of more than one bacterium for whatever reason.

O'Donnell in U.S. Pat. No. 5,702,701 discloses a process for treatment of soil and plants with a composition containing *Bacillus laterosporus*. The invention is limited in that it teaches use of a different microorganism.

Marrone et al. in U.S. Pat. No. 5,753,222 disclose an antibiotic-producing strain of *Bacillus* and methods of controlling plant diseases with it. The invention is limited in that it teaches use of a different microorganism.

Handelsman et al. in U.S. Pat. No. 5,852,054 disclose fungicidal toxins from a biocontrol bacterium. The invention is limited in that it teaches use of a different microorganism.

Marrone et al. in U.S. Pat. No. 5,869,042 disclose methods for controlling above-ground plant diseases. The invention is limited in that it teaches use of different microorganisms for a different purpose.

Shetty in U.S. Pat. No. 5,882,641 discloses fruit pomice compositions and their uses. The invention is limited in that it teaches use of different microorganisms.

Howell in U.S. Pat. No. 5,882,915 discloses viridiol-deficient strains of *Trichoderma* virens and process for making and using biocontrol agents that contain them. The invention is limited in that it teaches use of different microorganisms.

Heins et al. in U.S. Pat. No. 5,906,818 disclose a *Bacillus mycoides* strain for controlling corn rootworm. The invention is limited in that it teaches use of a different microorganism for a different purpose.

Smith et al. in U.S. Pat. No. 5,916,029 disclose a process for producing seeds coated with a microbial composition. The invention is limited in that it teaches use of different microorganisms.

Marrone et al. in U.S. Pat. No. 5,919,447 disclose a strain of *Bacillus* for controlling plant disease. The invention is limited in that it teaches use of a different microorganism.

Herrera-Estrella et al. in U.S. Pat. No. 5,922,603 disclose a method for obtaining strains of *Trichoderma* sp. The invention is limited in that it teaches use of a different microorganism.

Cook et al. in U.S. Pat. No. 5,972,689 disclose methods and compositions for control of root diseases. The invention is limited in that it teaches use of different microorganisms.

Eastin in U.S. Pat. No. 5,974,734 discloses solid-matrix priming of seeds with microorganisms. The invention is limited in that it teaches use of different microorganisms.

Handelsman et al. in U.S. Pat. No. 5,998,196 disclose a method for suppressing disease using a novel *Bacillus cereus* strain. The invention is limited in that it teaches use of a different microorganism.

Germida et al. in U.S. Pat. No. 6,015,553 disclose a *Bacillus subtilis* strain for controlling pests. The invention is limited in that it teaches use of a different microorganism for a different purpose.

Logan et al. in U.S. Pat. No. 6,017,525 discloses a method of poultry house litter treatment. The invention is limited in that it teaches use of a different microorganism for a different purpose.

Handelsman et al. in U.S. Pat. No. 6,030,610 disclose a novel strain of *Bacillus cereus*. The invention is limited in that it teaches use of a different microorganism.

Handelsman et al. in U.S. Pat. No. 6,033,659 disclose a novel strain of *Bacillus cereus*. The invention is limited in that it teaches use of a different microorganism.

Heins et al. in U.S. Pat. No. 6,103,228 discloses compositions and methods for controlling plant pests and a novel strain of *Bacillus subtilis*. The invention is limited in that it teaches use of a different microorganism.

Ocamb et al. in U.S. Pat. No. 6,133,196 disclose contacting conifer seeds with a culture of certain bacteria, drying the seeds, planting the seeds and then treating the plant growth medium with a certain ectomycorrhizal fungus (*Hebeloma* spp.). The reference does not teach treating seeds with a composition comprising a fungus and a bacterium.

Branly et al. in U.S. Pat. No. 6,232,270 discloses agricultural compositions containing bacteria. The invention is limited in that it teaches use of different microorganisms and a different process for their use. While the patent suggests that one bacterium that is useful within the disclosed invention is *Bacillus amyloliquefaciens*, it teaches that spores, cultures or suspensions of the bacterium must be combined with an agriculturally effective ingredient of a plant growth stunting agent or herbicide.

Moesinger in U.S. Pat. No. 6,326,016 discloses plant immunization compositions. The invention is limited in that it teaches use of different microorganisms and a different process for their use. While the patent suggests that one bacterium that can be used according to the disclosed invention is *Bacillus amyloliquefaciens*, and that one fungus that can be used according to the invention is *Trichoderma* spp., it teaches production of an extract by means of biotechnological fermentation process performed by only one microorganism. Furthermore, the patent teaches that high-temperature autoclaving (e.g., one hour at +120 degrees C.) and (optionally) filtering are further steps in preparation of the extract.

Background art is also disclosed in the non-patent literature. The StratSoy Research Database posted on the Web (apparently in 1996) a description of a research project entitled Interaction of Soybean Roots with Soilbome Pathogens and Nonpathogens. The project studied the use of *Bacillus amyloliquefaciens* B94 as a biocontrol agent for plant diseases. The invention is limited in that it teaches use of a single different microorganism.

An article entitled Seed's Coat of Many Microbes Wards Off Rot in Science Update section of the April, 1997, issue of Agricultural Research, disclosed the mixing of helpful fungi and bacteria to weaken or kill fungal pathogens that attack young corn sprouts. The applicant believes that the combination used was *T. virens* and *Pseudomonas cepacia*. This invention is limited for two reasons: (1) *P. cepacia* is implicated as causative in deaths in cystic fibrosis patients and, therefore, EPA registration would probably not be possible, and (2) *P. cepacia* is not a spore-forming bacterium and, therefore, the moisture content of the combination must be maintained at greater than about 17 percent. *T. virens* can be stored and applied at low moisture levels and does not remain in the spore state at the higher moisture levels, making its combination with *P. cepacia* impractical.

In an article authored by L. E. Datnoff et al. entitled Effect of Bacterial and Fungal Microorganisms to Colonize Tomato Roots, Improve Transplant Growth and Control *Fusarium* Crown and Root Rot that was posted on the Web in 2000 by the University of Florida Southwest Florida Research and Education Center, the authors discuss using a combination of an unidentified bacterial strain and *Gliocladium virens* to control *Fusarium* root rot. The invention is limited in that it teaches use of different microorganisms.

The U.S. Environmental Protection Agency Office of Pesticide Programs posted a Biopesticide Fact Sheet on *Bacillus subtilis* var. *amyloliquefaciens* strain FZB24 (006480) in May, 2000. The fact sheet noted that the strain was approved for use as a growth enhancer and disease suppressor. The invention is limited in that it does not teach the use of a fungal/bacterial combination.

No single reference and no combination of the references teach the invention disclosed herein. The background art does not teach combinations of microorganisms disclosed herein, combinations that provide a surprising consistency of performance in plant disease control.

BRIEF SUMMARY OF THE INVENTION

A purpose of the invention is to control the plant pathogens that cause early and late season root and stalk rot. Another purpose is to provide for season-long protection for plants from the pathogens that cause early and late season root and stalk rot. Another purpose is to provide consistent disease control for plants. Yet another purpose is to increase the yield of plants and plant seed production.

One advantage of the invention is that root and stalk rot can be controlled with a composition that is not toxic to humans. Another advantage of the invention is that root and stalk rot can be controlled more economically than with chemical fungicides. Yet another advantage of the invention is that it provides a biocontrol agent or bio-pesticide with extended shelf life. Thus, a seed can be treated with the biocontrol agent and stored for a period of months and still host a viable biocontrol agent that will colonize the root when the seed is placed in the ground, germinates and grows. Furthermore, the disclosed biocontrol agent is competitive with natural soil microbes that occur in the rhizosphere while providing pathogen protection for the plant. A further advantage of the invention is that the combination of a fungal/bacterial antagonist is more effective in controlling fungal pathogens in the plant rhizosphere than either a fungal antagonist or a bacterial antagonist alone. Thus, the invention provides an easy-to-use, effective means of controlling plant pathogens that have been only been controllable by rotation management. A further advantage of the invention is that its use produces more consistent results than the use of either a fungal antagonist or a bacterial antagonist alone, as shown by the Working Examples presented herein. In fact, use of the antagonist combinations disclosed herein is shown to be functional when use of its individual constituent antagonists is not.

The compositions disclosed herein may be integrated into Integrated Pest Management (IPM) programs, the inventive compositions may be used in combination with other management systems. As an alternative to synthetic agents, biocontrol agents (bio-pesticides) offer the advantage of containing naturally derived constituents that are safe to both humans and the environment. Specifically, bio-pesticides offer such advantages as being inherently less toxic than conventional pesticides, generally affecting only the target pest and closely related organisms, and are often effective in very small quantities. For these reasons, bio-pesticides often decompose quickly and, therefore, are ideal for use as a component of Integrated Pest Management (IPM) programs.

The applicant has shown through a variety of laboratory and field trials that *Bacillus subtilis* var. *amyloliquefaciens* TJ 1000 and *Trichoderma virens* G1-3 are compatible with one another and that they act synergistically to consistently produce increased yield in plants. These results were presented in the parent application referenced above.

Field trials were conducted as part of the applicant's continuing research effort that tested other known *Bacillus subtilis* var. *amyloliquefaciens* (*Bacillus amyloliquefaciens*) strains and other known *Trichoderma virens* isolates. The purpose of testing was to determine whether the surprising synergism between a *Bacillus subtilis* var. *amyloliquefaciens* bacterium and a *Trichoderma virens* fungus disclosed in the parent application would be present between other strains and isolates of the same genus and species.

This testing by the applicant did result in the discovery of a synergistic activity between other isolates and strains of *Trichoderma virens* and *Bacillus subtilis* var. *amyloliquefaciens*. These results are presented in the final three working examples at the end of this document. The results show that other isolates of *Trichoderma virens* and other strains of *Bacillus subtilis* var. *amyloliquefaciens* do have synergistic properties. The applicant's research has also confirmed that the combination of *T. virens* G1-3 and *Bacillus subtilis* var. *amyloliquefaciens* TJ 1000 is superior to combinations comprising any other tested strains, but that synergies among other combinations do exist. These synergies have led the applicant to the conclusion that his patent rights should include combinations of all *Trichoderma virens* isolates and all *Bacillus subtilis* var. *amyloliquefaciens* strains.

The invention is an inoculum, a seed coated with the inoculum, a plant protected with the inoculum, a method of producing the inoculum and a method of protecting a seed or a plant with the inoculum. A further embodiment of the inoculum comprises a combination of a fungus and a bacterium. Preferably, the fungus is a species of *Trichoderma* and the bacterium is a species of *Bacillus*, preferably a spore-forming strain of *Bacillus*. More preferably, the fungus is *Trichoderma virens* and the bacterium is *Bacillus subtilis* var. *amyloliquefaciens*, although other combinations are also envisioned. Even more preferably, the fungus is *Trichoderma virens* G1-3 (ATCC 58678) or *Trichoderma virens* G1-21 (an isolate that is commercially available from Thermo Trilogy Corporation) and the bacterium is *Bacillus subtilis* var. *amyloliquefaciens* TJ1000 or 1BE (ATCC BAA-390) or *Bacillus subtilis* var. *amyloliquefaciens* FZB24 (a strain that is commercially available from Earth Biosciences, Inc.).

Further embodiments of the invention comprise combining of a *Trichoderma virens* fungus and a *Bacillus amyloliquefaciens* bacterium and placing this combination on a seed or in the vicinity of the seed or seedling. A person having ordinary skill in the art would understand that the names *Trichoderma virens* and *Gliocladium virens* are synonymous. The ATCC listing of this organism under ATCC Accession No. 58678 confirms its prior classification as *Gliocladium virens*.

In a further embodiment, the inoculum is produced by adding an essentially pure culture, a substantially pure culture, an axenic culture or a biologically pure culture of *Trichoderma virens* to a bioreactor containing molasses-yeast extract growth medium using a standard inoculation technique. The medium is agitated and aerated and its temperature is maintained at about 28 degrees Centigrade. After the *Trichoderma virens* is grown in the medium for about eight hours, an essentially pure culture, a substantially pure culture, an axenic culture or a biologically pure culture of *Bacillus amyloliquefaciens* is added to the medium using a standard inoculation technique. The combined, competitive culture is grown under the aforementioned conditions and produces maximum cell and spore counts in approximately seven days. The combined culture is then used as an inoculum and is applied each seed at a rate of no less than about 1,000 spore counts per seed.

In a further embodiment, a solution containing an essentially pure culture, a substantially pure culture, an axenic culture or a biologically pure culture of the fungal antagonist *Trichoderma virens* is combined with a solution containing an essentially pure culture, a substantially pure culture, an axenic culture or a biologically pure culture of *Bacillus amyloliquefaciens* in a 50/50 mixture by volume and is applied to a seed at a rate of no less than about 10,000 spore counts per seed.

In a preferred embodiment, the invention is an agricultural inoculum suitable for inoculating plant seeds comprising a *Trichoderma virens* fungal antagonist selected from the group consisting of isolate ATCC 58678, isolate G1-21 and mutants thereof; a *Bacillus subtilis* var. *amyloliquefaciens* bacterial antagonist selected from the group consisting of strain ATCC BAA-390, strain FZB24 and mutants thereof, and a suitable carrier that is non-phytotoxic, non-bacteriostatic, and non-bactericidal. Suitable carriers include wettable clay based powders, dextrose granules or powders, sucrose granules or powders and maltose-dextrose granules or powders.

A further embodiment of the invention is a composition of matter comprising a plant seed inoculated with a combination comprising a *Trichoderma virens* antagonist selected from the group consisting of isolate ATCC 58678, isolate G1-21 and mutants thereof and a *Bacillus amyloliquefaciens* antagonist selected from the group consisting of strain ATCC BAA-390, strain FZB24 and mutants thereof, wherein said combination suppresses growth of plant pathogenic fungi.

Yet a further embodiment of the invention is a seed or plant inoculated with a combination selected from the group consisting of: a *Trichoderma virens* antagonist selected from the group consisting of isolate G1-21 and mutants thereof and a *Bacillus amyloliquefaciens* antagonist selected from the group consisting of strain FZB24 and mutants thereof; a *Trichoderma virens* antagonist selected from the group consisting of isolate ATCC 58678 and mutants thereof and a *Bacillus amyloliquefaciens* antagonist selected from the group consisting of strain FZB24 and mutants thereof, and a *Trichoderma virens* antagonist selected from the group consisting of isolate ATCC 58678 and mutants thereof and a *Bacillus amyloliquefaciens* antagonist selected from the group consisting of strain FZB24 and mutants thereof, wherein the combination suppresses growth of plant pathogenic fungi.

In another preferred embodiment, the invention is a method of protecting a plant from disease caused by a plant pathogenic fungus comprising inoculating seeds from said plant with a combination comprising a *Trichoderma virens* fungal antagonist selected from the group consisting of isolate ATCC 58678, isolate G1-21 and mutants thereof and a *Bacillus amyloliquefaciens* bacterial antagonist selected from the group consisting of strain ATCC BAA-390, strain FZB24 and mutants thereof, wherein said combination suppresses growth of plant pathogenic fungi.

A further embodiment of the invention is a method of protecting a seed or a plant from disease caused by a plant pathogenic fungus comprising inoculating seeds from said plant with a composition comprising a *Trichoderma virens* fungal antagonist and a *Bacillus amyloliquefaciens* bacterial antagonist. Preferably, the fungal antagonist is selected from the group consisting of isolate ATCC 58678, isolate G1-21 and mutants thereof and the bacterial antagonist is selected from the group consisting of strain ATCC BAA-390, strain FZB24 and mutants thereof.

A further embodiment of the invention is a method of protecting a seed or a plant from disease caused by a plant pathogenic fungus comprising inoculating seeds from said plant with a composition comprising a fungal antagonist and a bacterial antagonist, wherein said combination suppresses growth of plant pathogenic fungi. A further embodiment is capable of control of the plant pathogen fungi *Fusarium, Phythium, Phytophthora* and *Penicillium*.

A further embodiment of the invention is a method of protecting a plant from disease caused by a plant pathogenic fungus comprising inoculating seeds from said plant with a composition selected from the group: a composition comprising a *Trichoderma virens* fungal antagonist selected from the group consisting of isolate ATCC 58678 and mutants thereof and a *Bacillus amyloliquefaciens* bacterial antagonist selected from the group consisting of strain ATCC BAA-390 and mutants thereof, and a composition comprising a *Trichoderma virens* fungal antagonist selected from the group consisting of isolate G1-21 and mutants thereof and a *Bacillus amyloliquefaciens* bacterial antagonist selected from the group consisting of strain FZB24 and mutants thereof, wherein said combination suppresses growth of plant pathogenic fungi.

Yet a further embodiment of the invention is a method for biologically controlling or inhibiting stalk rot or root rot comprising coating seeds with an effective amount of a composition comprising a *Trichoderma virens* isolate G1-21 and mutants thereof and a *Bacillus amyloliquefaciens* strain FZB24.

A further embodiment of the invention is process for making a composition comprising introducing an essentially pure culture of *Bacillus amyloliquefaciens* (strain FZB24) to a growth medium about eight hours after an essentially pure culture of *Trichoderma virens* (isolate G1-21) is introduced to the growth medium and growing the culture as a competitive culture.

A further embodiment of the invention is a process comprising making a composition by combining an essentially pure culture of *Trichoderma virens* G1-3 (isolate G1-21) with an essentially pure culture of *Bacillus amyloliquefaciens* (strain FZB24) in a 50:50 mixture and applying said composition to a seed at a rate of at least 100,000 spores per seed.

In one embodiment of the invention disclosed herein, the spore count applied per seed ranges from about 1,000 to about 1,000,000, regardless of seed size. In another embodiment of the invention, the spore count per seed is from about 1,000 to about 10,000. In a further embodiment of the invention, the spore count per seed is from about 10,000 to about 100,000. In a yet further embodiment of the invention, the spore count per seed is from about 100,000 to about 1,000,000. In a yet another embodiment of the invention, the spore count per seed is from about 1,000,000 to about 2,000,000.

A further embodiment of the invention is a method for protecting plants in a growing medium from damping off and root rot fungal plant disease comprising placing in the growing medium in the immediate vicinity of the plant to be protected an effective quantity of one of the fungal/bacterial combinations disclosed herein.

Yet a further embodiment of the invention is a method for protecting plants from fungal plant disease comprising adding one of the fungal/bacterial combinations disclosed herein in an effective quantity to a substrate such as pelletized calcium sulfate or pelletized lime and placing the pellet in the immediate vicinity of the plant to be protected. The pellet may or may not contain other nutrients.

A further embodiment of the invention is a method for protecting plants from fungal plant disease comprising adding one of the fungal/bacterial combinations disclosed herein in an effective quantity to a liquid solution such as water and applying the liquid solution in the immediate vicinity of the plant to be protected. The liquid may or may not contain additional nutrients and may include a chemical fungicide applied to the seed such as, for example, Maxim or captan. The disclosed combination may also be added to a plant nutrient (nitrogen-phosphorus-potassium (NPK)) plus plant micro-nutrient solution that is compatible with the combination and applied as an in-furrow treatment.

A further embodiment of the invention is a method for biologically controlling a plant disease caused by a plant-colonizing fungus, the method comprising inoculating a seed of the plant with an effective amount of a microbial inoculant comprising a combination of microorganisms having all of the identifying characteristics of *Trichoderma virens* and *Bacillus amyloliquefaciens*, said inoculation resulting in the control of said plant disease. The invention is also a method according to the above further embodiment wherein said inoculation results in the control of more than one plant disease.

Yet a further embodiment of the invention involves combining a *Trichoderma virens* fungal antagonist and a *Bacillus amyloliquefaciens* bacterial antagonist to enhance ease of use and longevity of shelf life both as a stored product and when applied to a seed. In a further embodiment, the invention involves applying the disclosed *Trichoderma* microorganism and the *Bacillus* microorganism to a wettable powder, in which form it is applied.

A further embodiment of the invention is composition of matter made by combining: a composition made by combing a plurality of antagonists selected from the group consisting of a *Trichoderma virens* antagonist selected from the group consisting of isolate G1-21 and mutants thereof and a *Bacillus amyloliquefaciens* antagonist selected from the group consisting of strain FZB24 and mutants thereof; a *Trichoderma virens* antagonist selected from the group consisting of isolate ATCC 58678 and mutants thereof and a *Bacillus amyloliquefaciens* antagonist selected from the group consisting of strain FZB24 and mutants thereof; and a *Trichoderma virens* antagonist selected from the group consisting of isolate ATCC 58678 and mutants thereof and a *Bacillus amyloliquefaciens* antagonist selected from the group consisting of strain FZB24 and mutants thereof; and a suitable carrier that is non-phytotoxic, non-bacteriostatic, and non-bactericidal.

A further embodiment of the invention is an antagonist for controlling plant pathogens made by combining effective amounts of: a fungal antagonist selected from the group of *Trichoderma virens* isolate (isolate G1-21) and mutants thereof; a bacterial antagonist selected from the group of *Bacillus amyloliquefaciens* (strain FZB24) and mutants thereof; and a suitable carrier that is non-phytotoxic, non-bacteriostatic, and non-bactericidal. Preferably, the antagonist made by further combining with the antagonist an effective amount of another bacterial strain.

Yet a further embodiment of the invention is a seed assembly made by combining a plant seed with effective amounts of a *Trichoderma virens* fungal antagonist and a *Bacillus subtilis* var. *amyloliquefaciens* bacterial antagonist. In a further embodiment, the seed is a seed of a plant selected from the group of a monocot, and a dicot. In a further embodiment, the seed is a seed of a plant selected from the group of a legume plant, and a non-legume plant. In a further embodiment, the seed is a seed of a plant selected from the group of corn, sunflower, soybean, field pea, and wheat.

A further embodiment of the invention is method for culturing a plant comprising: applying an antagonist disclosed herein to a seed or to the seedbed of the plant; planting the seed in the seedbed; growing the plant to yield a crop; and harvesting the crop; wherein said applying step increases the yield of the crop. In a further embodiment, the antagonist is applied to the seed or to the seedbed of a plant selected from the group of a monocot, and a dicot. In a further embodiment, the antagonist is applied to the seed or to the seedbed of a plant selected from the group of a legume plant, and a non-legume plant. In a further embodiment, the antagonist is applied to the seed or to the seedbed of a plant selected from the group of corn, sunflower, soybean, field pea, and wheat.

Plant species that may be treated with the disclosed invention include commercial crops species, e.g., barley, oat, millet, alfalfa. The disclosed invention may also be used to treat leguminous plants (e.g., soybeans, alfalfa, and peas) and non-leguminous plants (e.g., corn, wheat, and cotton). The disclosed invention may also be used to treat angiosperms and cereals.

Yet a further embodiment is a process comprising: making a composition by combining an essentially pure culture of *Trichoderma virens* (isolate G1-21) with an essentially pure culture of *Bacillus amyloliquefaciens* (strain FZB24) in a mixture; and applying said composition to a seed; wherein said mixture ranges in composition from 10 to 90 percent *Trichoderma virens* (isolate G1-21) by volume and from 90 to 10 percent *Bacillus amyloliquefaciens* (strain FZB24) by volume.

Yet a further embodiment of the invention is a process comprising: making a composition by combining an essentially pure culture of *Trichoderma virens* (isolate G1-21) with a plurality of essentially pure cultures of bacteria in a mixture; and applying said composition to a seed; wherein said mixture ranges in composition from 10 to 90 percent *Trichoderma virens* (isolate G1-21) by culture volume.

In one embodiment of the invention the mixture ranges in composition from 10 to 90 percent *Trichoderma virens* by volume and from 90 to 10 percent *Bacillus amyloliquefaciens* by volume. In another embodiment of the invention, the mixture comprises about 20 percent *Trichoderma virens* by volume 80 percent *Bacillus amyloliquefaciens* by volume. In a further embodiment of the invention, the mixture comprises about 30 percent *Trichoderma virens* by volume 70 percent *Bacillus amyloliquefaciens* by volume. In a yet further embodiment of the invention, the mixture comprises about 40 percent *Trichoderma virens* by volume 60 percent *Bacillus amyloliquefaciens* by volume.

A further embodiment of the invention is an antagonist for controlling plant pathogens made by combining effective amounts of: a fungal antagonist selected from the group of an isolate of *Trichoderma virens* and mutants thereof; a bacterial antagonist selected from the group a strain of *Bacillus amyloliquefaciens* and mutants thereof; and a suitable carrier that is non-phytotoxic, non-bacteriostatic, and non-bactericidal. Preferably, the isolate is *Trichoderma* virens (isolate G1-21), which is presently EPA registered.

In a further embodiment, the invention is an antagonist for controlling plant pathogens made by combining effective amounts of: a fungal antagonist selected from the group of *Trichoderma virens* (isolate G1-21) and mutants thereof; a plurality of bacterial antagonists; and a suitable carrier that is non-phytotoxic, non-bacteriostatic, and non-bactericidal. Preferably, the plurality of bacterial antagonists comprises a strain of *Bacillus lentimorbus*.

In a preferred embodiment, the invention is a method comprising: combining a spore-forming fungal strain and a spore-forming bacterial strain to produce a product comprising a composition of matter disclosed herein; and applying the product to a plant or to a part of the plant; whereby application of the product produces yield enhancement in the plant.

In another preferred embodiment, the invention is a method comprising: applying a *Trichoderma* spp. microorganism and a *Bacillus* spp. microorganism to a wettable powder to produce a combination comprising an antagonist disclosed herein; and applying the combination to a seed; whereby application of the combination produces a positive yield response in a plant growing from the seed.

In yet another preferred embodiment, the invention is a process comprising: making a composition of matter disclosed herein; and applying said composition of matter to a seed; wherein said composition of matter ranges in composition from 1 to 99 percent *Trichoderma* virens by culture volume and from 99 to 1 percent *Bacillus amyloliquefaciens* by culture volume.

In another preferred embodiment, the invention is a composition of matter comprising: a plant seed inoculated with an agricultural inoculum disclosed herein; wherein said combination increases the yield of the plant. In another preferred embodiment, the invention is a method for increasing the yield of a plant, the method comprising: coating a seed of the plant with an effective amount of an agricultural inoculum disclosed herein; and culturing the plant.

In another preferred embodiment, the invention is a composition made by combining effective amounts of: a spore-forming fungal antagonist; and a spore-forming bacterial antagonist; wherein the spore-forming fungal antagonist does not produce a substance that substantially inhibits the growth of the spore-forming bacterial antagonist and the spore-forming bacterial antagonist does not produce a substance that substantially inhibits the growth of the spore-forming fungal antagonist; and wherein the composition is effective at increasing the yield of a plant grown from a seed to which the composition has been applied. Preferably, the composition is effective at increasing the manganese content of the plant.

The compositions of the present invention can be used for controlling fungal infestations by applying an effective amount of the composition or a formulation thereof, either at one point in time or throughout the plant/crop cycle via multiple applications. The formulation may be applied to the locus to be protected for example by spraying, atomizing, vaporizing, scattering, dusting, coating, watering, squirting, sprinkling, pouring, fumigating, and the like. The dosage of the bioagent(s) applied may be dependant upon factors such as the type of fungal pest, the carrier used, the method of application (e.g., seed, plant application or soil delivery) and climate conditions for application (e.g., indoors, arid, humid, windy, cold, hot, controlled), or the type of formulation (e.g., aerosol, liquid, or solid).

Biocontrol agents comprising the disclosed compositions may be applied in agricultural, horticultural and seedling nursery environments. This generally includes application of agents to soil, seeds, whole plants, or plant parts (including, but not limited to, roots, tubers, stems, flowers and leaves). Bio-pesticide or microbial combinations may be used alone, however, they may additionally be formulated into conventional products such as dust, granule, microgranule, pellet, wettable powder, flowable powder, emulsion, microcapsule, oil, or aerosol. To improve or stabilize the effects of the bio-pesticide, the agent may be blended with suitable adjuvants and then used as such or after dilution if necessary.

A worker skilled in the art would recognize that the bioagent(s) may be formulated for seed treatment either as a pretreatment for storage or sowing. The seed may form part of a pelleted composition or, alternatively, may be soaked, sprayed, dusted or fumigated with the inventive compositions. Additionally, the inventive compositions may be applied to the soil or turf, a plant, crop, or a plantation. Some areas may additionally require that the invention provide for slow-release materials such that the agent is designed to have an extended release period.

In use, the invention disclosed herein may comprise the application of an aqueous or a non-aqueous spray composition to the crop. For example, the inventive composition may be applied to the soil, or to a plant part (e.g., stalk, root or leaf), or both, as an aqueous spray containing spray adjuvants such as surfactants and emulsified agricultural crop oils which insure that the agent is deposited as a droplet which wets the stalk or leaf and is retained on the plant so that agent can be absorbed.

The skilled artisan would realize that the inventive compositions may be applied in combination with nutrients (fertilizers) or herbicides or both, or may form part of a formulation comprising the inventive composition in combination with a fertilizer or herbicide or both. Such a formulation may be manufactured in the form of a liquid, a coating, a pellet or in any format known in the art.

The skilled artisan would realize that the inventive compositions may be applied to seeds as part of stratification, desiccation, hormonal treatment, or a mechanical process to encourage germination or to terminate dormancy. Treatments including the inventive agents in combination with hormones, PEG, or varying temperature, or in combination with mechanical manipulation of the seed (i.e. piercing), are contemplated.

Further aspects of the invention will become apparent from consideration of the drawings and the ensuing description of further embodiments of the invention. A person skilled in the art will realize that other embodiments of the invention are possible and that the details of the invention can be modified in a number of respects, all without departing from the inventive concept. Thus, the following drawings and description are to be regarded as illustrative in nature and not restrictive.

BRIEF DESCRIPTION OF THE DRAWINGS

The features of the invention will be better understood by reference to the accompanying drawings which illustrate presently further embodiments of the invention. In the drawings:

FIG. 1 is a plot that compares the incidence of stalk rot in TJ1300-treated plots versus the incidence of stalk rot in control plots.

FIG. 2 is a plot that compares final plant populations in TJ1300-treated plots versus final plant populations in control plots.

DETAILED DESCRIPTION OF THE INVENTION

A preferred embodiment of the invention comprises the fungus *Trichoderma virens* isolate G1-3 (ATCC 58678) or other isolates. These microorganisms may be obtained from the American Type Culture Collection (ATCC), 12301 Parklawn Drive, Rockville, Md., 20852-1776 and other culture collections or isolated from nature.

Another preferred embodiment of the invention comprises *Trichoderma* (*Gliocladium*) *virens* isolate G1-21 which is being marketed under the trademark SoilGuard® 12G by Thermo Trilogy Corporation, 9145 Guilford Road, Suite 175, Columbia, Md. 21046.

A further embodiment of the invention also comprises the bacterium *Bacillus lentimorbus* TJ 1000, which is renamed herein *Bacillus amyloliquefaciens* TJ1000 or 1BE, based on a more accurate determination of the name of *Bacillus* species that occurred before the parent patent application was filed. This microorganism was deposited with the ATTC on Oct. 31, 2001, and was assigned accession number ATCC BAA-390. Alternative embodiments of the invention comprise other strains which can be isolated from nature or obtained from ATCC or other culture collections.

Another preferred embodiment of the invention is comprised of *Bacillus subtilis* var. *amyloliquefaciens* strain FZB24 which is being marketed under the trademark Tae-gro® by Earth Bioscience, Inc., 26 Sherman Court, PO Box 764, Fairfield, Conn. 06430.

A further embodiment of the invention involves combining an essentially pure culture of *Trichoderma virens* and an essentially pure culture of *Bacillus amyloliquefaciens* in a competitive culture process. The competitive culture process involves adding the *Bacillus amyloliquefaciens* to a growth medium about eight hours after the *Trichoderma virens* was added to the medium. The combined culture is then applied to a seed, for example, a corn seed. The combination grown in a competitive culture provides protection for seeds and plants and is especially effective in a high-stress, high-fungal pathogen environment during the early stages of plant development.

A further embodiment of the invention involves growing an essentially pure culture of *Trichoderma virens* and an essentially pure culture of *Bacillus amyloliquefaciens* TJ1000 separately for five days. After the cultures are grown separately, the compositions that contain them are combined in a 50/50 combination by volume and then the combination is applied to a seed, for example, a corn seed. The combined cultures are applied to a seed provides protection for seeds and plants from fungal pathogens. This combination is especially effective under conditions that are less stressful to the plant.

A further step in the process involves applying either of the above combinations to a seed involves adding an aqueous solution comprising 30 grams/liter of molasses to the solution containing the combination to produce an appropriate spore count in the resulting composition. The resulting composition is then applied to the seed as a liquid mist to achieve optimum application rates per seed using the molasses as an adhesive to adhere the spores to the seed.

In a further embodiment, the bioreactor used to culture the microorganism cultures is a New Brunswick Bioflow III bioreactor. For optimal results, the agitation setting of the bioreactor is set at about 350 rpm, the aeration setting of the bioreactor is set at about 3.0 with an aeration air pressure of about 15 pounds per square inch and the temperature setting is set at about 28 degrees Centigrade. The further growth medium for each of the individual cultures and the combined competitive culture comprises about 30 grams per liter of molasses and about 5 grams per liter of yeast extract and is referred to as a MYE medium. In A further embodiment, the medium contains about 5 milliliters of antifoam. In a further embodiment, spore production is measured by counting spores using a hemacytometer manufactured by Hausser Scientific.

A variety of seed treatments or no seed treatment may be practiced before the seed is inoculated with the disclosed inoculum. In some further embodiments, seed treatments include osmotic priming and pre-germination of the seed. Because *Trichoderma virens* and *Bacillus amyloliquefaciens* are spore formers, the disclosed inoculum does not require high moisture levels for survival and, therefore, can be applied to seed and other materials without a sticker, such as those sold under the trade names Pelgel (LipaTech), Keltrol (Xanthan) Cellprill or Bond.

In a further embodiment, the invention involves combining of a spore forming fungal strain and a spore forming bacterial strain to enhance ease of use and longevity of shelf life both as a stored product and when applied to a seed. In A further embodiment, the invention involves applying the disclosed *Trichoderma* microorganism and the disclosed *Bacillus* microorganism to a wettable powder, and marketing the wettable powder.

First Greenhouse Working Example

Greenhouse testing was conducted to determine the effectiveness of the disclosed biocontrol agents. Treated and untreated corn seeds were grown in soil infested with seven percent *Fusarium* infested wheat seed. In this testing, the following treatment codes were used:

CONTROL—Nothing on the seed

TJ 1000—*Bacillus amyloliquefaciens* TJ 1000 or 1 BE

TJ 0300—*Trichoderma virens* G1-3

TJ 1300—50/50 combination of *Trichoderma virens* G1-3 and *Bacillus amyloliquefaciens* TJ1000 or 1BE TJ 1310—competitive culture of *Trichoderma virens* G 1-3 and *Bacillus amyloliquefaciens* TJ1000 or 1BE, resulting in a 70/30 ratio of *Trichoderma* to *Bacillus*

The results of greenhouse testing are presented in Table 0. The rating scale used was 9=worst plant protection and 1=best plant protection. Seed treated with biocontrol organisms grown in competitive culture showed an increase in plant protection over seed treatments with the same biological control organisms grown in non-competitive culture. The biocontrol agents were applied to the seed without a sticker.

TABLE 0

| | Greenhouse Testing Results | | | |
|---|---|---|---|---|
| Treatment | Replication 1 | Replication 2 | Replication 3 | Average |
| Control | 9 | 7 | 6 | 7.3 |
| TJ 0300 | 6 | 5 | 5 | 5.3 |
| TJ 1000 | 7 | 6 | 5 | 6 |
| TJ 1300 | 6 | 5 | 6 | 5.6 |
| TJ 1310 | 1 | 3 | 3 | 2.3 |

Field Trials Working Example

In a subsequent experiment, field trials were conducted at seven locations throughout the U.S. Site locations included Arizona, Colorado, Kansas, Montana, North Dakota and two South Dakota locations. At each location, the trial contained a CONTROL that was treated with the industry-standard chemical treatment, MAXIM. All cultures used in the trial were grown in MYE broth for five days. *Bacillus amyloliquefaciens* TJ1000 or 1BE was cultured individually (non-competitive) and with *Trichoderma virens* G1-3 (competitive culture). *Trichoderma virens* G 1-3 and *Bacillus*

*amyloliquefaciens* TJ 1000 or 1BE were also grown in non-competitive culture were also applied to the same seed to test the effectiveness of non-competitive culture versus competitive culture. Corn seeds were treated to give a final concentration of 1,000,000,000 bacterial/fungal spores per acre. Seed treatment was done with a Gustafson benchtop seed treater, Model BLT.

The plot location in Kansas was severely damaged by early dry conditions and the plot was terminated prior to harvest. The Colorado location was damaged due to machine damage prior to harvest. Colorado yield data were collected but were extremely variable and were not included in the analyzed data set. The Colorado stalk rot data were included in the data set.

The value of the Stalk Rot variable was determined by counting ten plants in a row, determining the number of root rot/stalk rot infected plants and expressing that number as a percentage. As illustrated in FIG. 1, in six trials, the average infection rate in the control was 55.13 percent versus 38.62 percent in the entries treated with the fungal/bacterial combination, TJ1300. The data revealed an average reduction of disease incidence of 30 percent with the Colorado location showing a reduction of over 60 percent.

Figure 2:
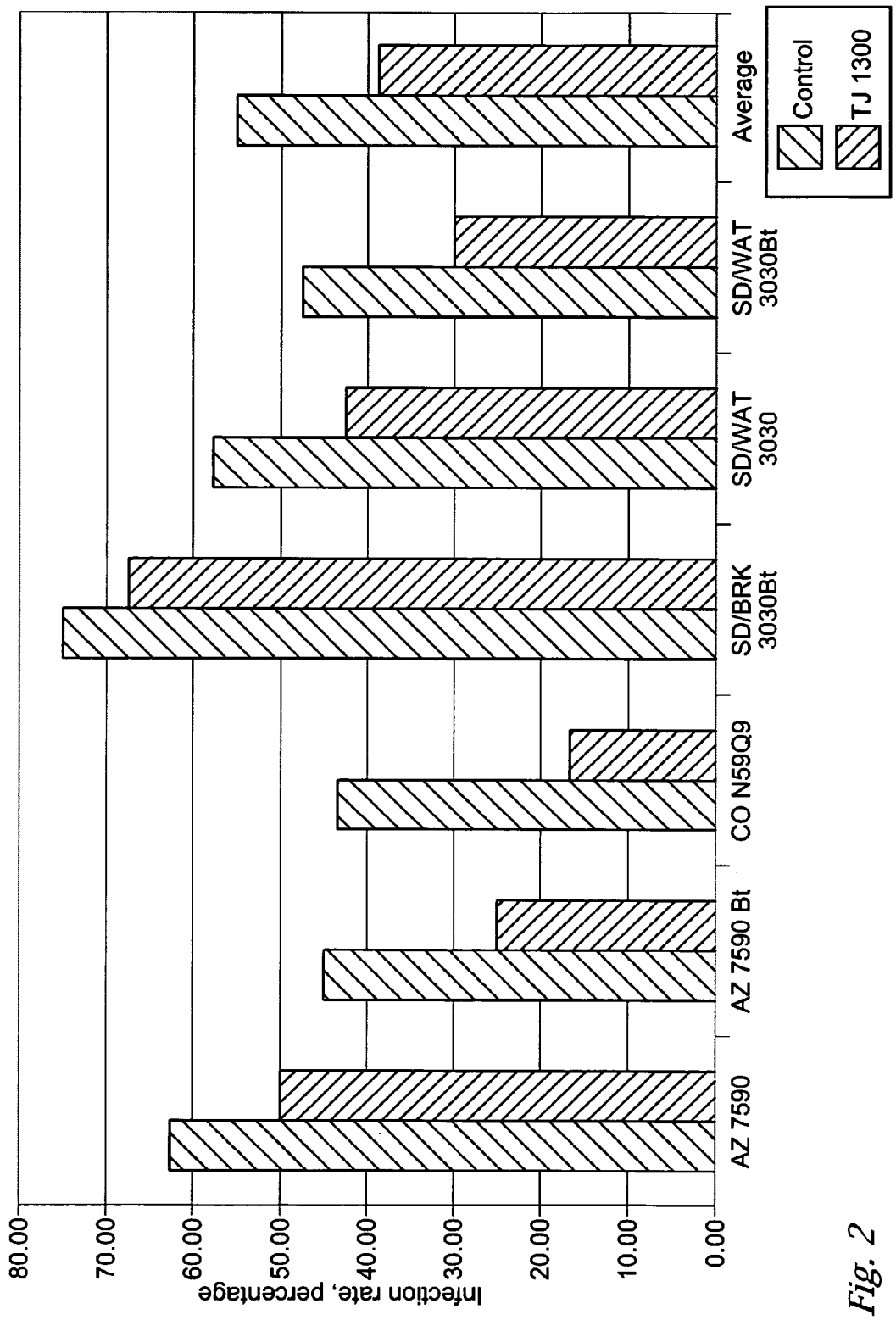

The value of the Final Population variable was determined by a conducting a physical count of the plants in a measured area and converting to a per acre count. As illustrated in FIG. 2, the average increase in final plant population was 3,742 plants per acre or an increase of 12.2 percent. This increased population was the result of controlling the disease early and having less plant death throughout the season.

Use of TJ1300 resulted in an average yield benefit of 5.35 bushels per acre. Average yield was determined from eight trials: 4 in South Dakota, 1 in North Dakota, 2 in Arizona, and 1 in Montana.

Second Greenhouse Working Example

Greenhouse Methods: All test cultures were grown in MYE (three percent Molasses, 0.5 percent Yeast Extract) broth for five days. Bacteria were grown up individually (non-competitive) and with *T. virens* G1-3 (competitive culture). *T. virens* G1-3 was also grown in a non-competitive culture for testing. *T. virens* G1-3 and test bacteria grown in non-competitive culture were also applied to the same seed to test the effectiveness of non-competitive culture versus competitive culture. Corn seeds were treated to give a final concentration of $1 \times 10^9$ bacteria/fungal spores (may also be referred to a Colony Forming Units or CFU) per acre. Seed treatment was done with a Gustafson Benchtop Seed Treater, Model BLT. Seeds were grown in soil infested with seven percent *Fusarium*-infested wheat seed. After four weeks, plant heights were taken as well as plant biomass. Plant heights were taken by measuring from the soil line to the tallest leaf, biomass of the plants was taken by cutting the plants at the soil line and then weighing plants on analytical scale. The treatment matrix was as follows:

Control—No pathogen added to soil.
Control—With pathogen added to soil.
TJ1000—*Bacillus amyloliquefaciens* TJ1000 or 1BE
TJ0300—*Trichoderma virens* G1-3
TJ2000—*Erwinia carotovora*
TJ1300—*B. amyloliquefaciens* TJ1000 or 1BE and *T. virens* G1-3 (non-competitive)
TJ2300—*E. carotovora* and *T. virens* G1-3 (non-competitive)
TJ 1310—*B. amyloliquefaciens* TJ 1000 or 1 BE and *T. virens* G 1-3 (competitive)
TJ1-2310—*B. amyloliquefaciens* TJ 1000 or 1 BE, *E. carotovora* and *T. virens* G 1-3 (competitive)
TJ23 10—*E. carotovora* and *T. virens* G 1-3 (competitive)

Determination of CFU (Colony Forming Units) concentrations in competitive cultures: Competitive cultures grown for five days. CFU counts of each organism were performed using a hemacytometer (Hausser Scientific) under light microscopy 5000× magnification. This method was used to determine the CFU counts in the greenhouse and field trials.

Enumeration through plate counts: Competitive cultures were grown for five days in submerged culture then 200 milliliters (ml) of the culture was harvested and aliquoted into four 50 ml centrifuge tubes. After centrifugation at 10,000 revolutions per minute (rpm) for 10 minutes resulting pellets were washed twice in equal volumes of $D_2H_2O$. Pellets were then re-suspended in 25 ml of saline. One ml samples were diluted $10^{-1}$ to $10^{-8}$ and plated onto potato dextrose agar (PDA) plates. Colonies are then counted and correlated with the dilution rates to determine CFU per ml of culture broth.

Results: All of the biocontrol agents in this experiment produced significant plant biomass increases over the pathogen-treated control and all of the treatments were numerically greater than the control plants in soil that contained no pathogen. The effects of bacterial/fungal combination TJ 1310 and the bacterial treatment TJ 1000 were significantly greater than both controls in the experiment.

TABLE 1

Demonstration of the Effectiveness of Biological Combinations and Individual Bacteria and Individual Fungal Treatments on Increasing the Biomass of Greenhouse-Grown Corn Seedlings in Pathogen-Treated Soil vs. the Untreated Control

| Treatment | Ratio | Rank | Biomass (grams) |
|---|---|---|---|
| Control Path | 0/0 | 10 | 3.62 a |
| Control No Path | 0/0 | 9 | 7.25 ab |
| TJ 1300 | 50/50 | 8 | 8.67 b |
| TJ 2310 | 30/70 | 7 | 9.04 b |
| TJ 2000 | 100/0 | 6 | 10.73 b |
| TJ 1-2310 | 20/20/60 | 5 | 11.37 b |
| TJ 2300 | 50/50 | 4 | 11.41 b |
| TJ 0300 | 0/100 | 3 | 11.53 b |
| TJ 1310 | 30/70 | 2 | 12.24 bc |
| TJ 1000 | 100/0 | 1 | 12.89 bc |
| CV % | | | 33.9 |
| LSD (0.05) | | | 4.55 |

Combinations Field Trial Working Example

Materials and Methods: A field trial was conducted using the corn variety NK 3030Bt using the following biological treatments of the seed at a rate of approximately $10^6$ CFU per seed. The seed was planted at a seeding rate of 25,000 seeds per acre in 30-inch rows in a randomized, replicated block. Each entry was replicated four times. The pathogen levels were natural populations at a location near Groton, S.Dak. The entries were as follows:

Control: Maxim Seed treatment (Maxim is a trademark of Syngenta Crop Protection)
TJ 1000—*Bacillus amyloliquefaciens* TJ1000 or 1BE
TJ 0300—*Trichoderma virens* G1-3
TJ 1300—50/50 combination of *B. amyloliquefaciens* TJ1000 or 1BE and *T. virens* G1-3
TJ 1310—Coculture 30/70 combination of *B. amyloliquefaciens* TJ 1000 or 1 BE and T. virens G1-3
TJ 66/300—50/50 combination of *Bacillus lentimorbus* and *T. virens* G1-3

Results: The trial produced significant yield response over the control with the entries TJ 0300, TJ 1300, and TJ 1310. The combinations TJ 1300 and TJ 1310 produced a yield response numerically greater than that of TJ 0300. The effects of bacterial/fungal combination TJ 66/300 and the bacterial treatment TJ 1000 were numerically greater than the control but not significantly greater. The results are presented in Table 2.

Conclusion: The bacterial/fungal combinations of entries TJ 1300 and TJ 1310 are the most effective biocontrol treatments in the trial for increasing the yield of corn.

TABLE 2

Effect of Biological Seed Treatment on Yield of Corn Variety N3030 Bt under Field Conditions.

| Treatment | Ratio | Rank | Location | Trial | Yield |
|---|---|---|---|---|---|
| Control Maxim | 0/0 | 6 | Groton, SD | Seed Treat | 164.8 a |
| TJ 1000 | 100/0 | 4 | Groton, SD | Seed Treat | 175.1 ab |
| TJ 0300 | 0/100 | 3 | Groton, SD | Seed Treat | 179.5 bc |
| TJ 1300 | 50/50 | 2 | Groton, SD | Seed Treat | 183.3 bc |
| TJ 1310 | 30/70 | 1 | Groton, SD | Seed Treat | 189.8 c |
| TJ 66/300 | 50/50 | 5 | Groton, SD | Seed Treat | 173.2 ab |
| CV % | | | | | 13.54 |
| LSD (0.05) | | | | | 12.5 |

50/50 Combination Field Trial Working Example

Materials and Methods: A field trial was conducted using the corn variety NK 3030Bt using the following biological treatments of the seed at a rate of approximately $10^6$ CFU per seed. The seed was planted at a seeding rate of 25,000 seeds per acre in 30-inch rows in a randomized replicated block. Each entry was replicated four times. The pathogen levels were natural populations at a location near Groton, S.Dak. The entries were as follows:

Control: Maxim Seed treatment (Maxim is a trademark of Syngenta Crop Protection)

TJ 1300-50/50 combination of *B. amyloliquefaciens* TJ1000 or 1BE and *T. virens* G1-3

Results: As indicated in Table 3, the trial produced a significant response in the yield of the seed treated with the biocontrol agent TJ 1300 (described above) as compared with the untreated control.

TABLE 3

Effect of Biological Seed Treatment on Yield of Corn Variety NK 3030Bt under Field Conditions.

| Treatment | Ratio | Rep | Location | Yield |
|---|---|---|---|---|
| Control | 0/0 | 1 | Groton, SD | 156.8 |
| Control | 0/0 | 2 | Groton, SD | 163.3 |
| Control | 0/0 | 3 | Groton, SD | 151.0 |
| Average | 0/0 | | Groton, SD | 157.03 a |
| 1300 | 50/50 | 1 | Groton, SD | 184.3 |
| 1300 | 50/50 | 2 | Groton, SD | 179.1 |
| 1300 | 50/50 | 3 | Groton, SD | 177.3 |
| Average | 50/50 | | Groton, SD | 180.21 b |
| CV % | | | | 5.65 |
| LSD (0.05%) | | | | 9.04 |

Application Rate Field Trial Working Example

Materials and Methods: A field trial was conducted using the corn variety NK2555 using the TJ 1300 (50/50) combination of *B. amyloliquefaciens* TJ1000 or 1BE and *T. virens* G1-3) biological treatments of the seed at variable rates. The purpose of the trial was to identify the most effective application rate for the bacterial/fungal combination of TJ 1300. The 1× rate was approximately $1 \times 10^6$ CFU per seed. The seed was planted at a seeding rate of 25,000 seeds per acre in 30-inch rows in a randomized, replicated block. Each entry was replicated four times. The pathogen levels were natural populations at a location near Groton, S.Dak. The entries were as follows:

Control—Maxim (Maxim is a trademark of Syngenta Crop Protection)
0.5× rate
1× rate
1.5× rate
2× rate Results: All of the biocontrol treatments in this experiment resulted in significant yield response over the control with the 1.5× rate producing significantly better results than the 2× rate. The results of this trial, presented in Table 4, indicated that the most efficacious application rate of the biocontrol agent TJ 1300 was approximately $1.5 \times 10^6$ per seed.

TABLE 4

Effect of TJ 1300 Biological Seed Treatment on Yield of Corn Variety N2555 at Variable Rates

| Treatment | Ratio | Rank | Location | Trial | Yield |
|---|---|---|---|---|---|
| Control | 0/0 | 5 | Groton, SD | Rate | 140.2 a |
| 0.5 × rate | 50/50 | 3 | Groton, SD | Rate | 153.6 bc |
| 1 × rate | 50/50 | 2 | Groton, SD | Rate | 156.2 bc |
| 1.5 × rate | 50/50 | 1 | Groton, SD | Rate | 161.1 c |
| 2 × rate | 50/50 | 4 | Groton, SD | Rate | 152.07 b |
| CV % | | | | | 5.31 |
| LSD (0.05%) | | | | | 8.61 |

Liquid Biocontrol Preparations Working Example

Materials and Methods: Field trials were conducted using the corn varieties NK 3030 and NK 3030Bt at a location in Brookings, S.Dak. and NK 3030Bt and NK2555 at a location in Groton, S.Dak. The purpose of the trial was to compare pathogen control of liquid biocontrol preparations to a control treated with only water. The results of the trial were quantified in yield of corn in bushels per acre. The water was applied to the control at a 10 gallon per acre rate. Biocontrol treatments were prepared by adding $1 \times 10^8$ CFU per gram of a wettable powder (Mycotech, Inc.). Two and one half grams of the wettable powder was added per one gallon of water and soil applied in the seed furrow at a rate of 10 gallons per acre. The seed was Maxim (Maxim is a trademark of Syngenta Crop Protection) treated and was planted at a seeding rate of 25,000 seeds per acre in 30-inch rows in a randomized, replicated block. Each entry was replicated four times. The pathogen levels were natural populations at each location. The entries were as follows:

Control—Water
TJ 1000—*Bacillus amyloliquefaciens* TJ 1000 or 1BE
TJ 0300—*Trichoderma virens* G1-3
TJ 1300—50/50 combination of *B. amyloliquefaciens* TJ1000 or 1BE and *T. virens* G1-3
TJ 1310—Coculture 30/70 combination of *B. amyloliquefaciens* TJ1000 or 1BE and T virens G1-3
TJ 66/300—50/50 combination of *Bacillus lentimorbus* and *T. virens* G1-3

Results: Table 5 shows a significant yield increase to the biocontrol treatments of TJ 1000, TJ1300, and TJ 66/300. All of the biocontrol treatments showed a numerical yield increase.

Table 6 shows a significant yield increase to the biocontrol treatments of TJ1000, TJ0300, and TJ1300. Again, all of the biocontrol treatments showed a numerical yield increase.

Table 7 shows no significance in the yield between the treatments and the control, however, the yield of TJ0300 was numerically less than the control by over 10 bushels per acre and is significantly less than the yields of the TJ1000 and TJ 1310 bacterial/fungal combination. This table demonstrates the strength of the disclosed bacterial/fungal combinations over the fungal control alone.

Table 8 shows the treatments of TJ 1000 and TJ 66/300 with significantly less yield than the control while the treatments of TJ0300, TJ1300, and TJ1310 having no significant difference. In this trial, it was the bacterial entry of TJ1000 alone that shows weakness in pathogen control. This table demonstrates the strength of disclosed bacterial/fungal combinations over the bacterial treatment alone.

Conclusion: The bacterial/fungal combination of entries TJ 1300 and TJ 1310 produce consistent pathogen control and/or yield response, while the bacteria entry of TJ 1000 alone and fungal entry of TJ 0300 alone produce inconsistent pathogen control and/or yield response.

TABLE 5

Liquid Drench Treatment on Corn Variety NK3030 at Brookings, SD Location

| Treatment | Variety | Ratio | Rank | Location | Trial | Yield |
|---|---|---|---|---|---|---|
| Control | NK3030 | 0/0 | 6 | Brookings, SD | Liquid | 162.2 a |
| TJ 1000 | NK3030 | 100/0 | 1 | Brookings, SD | Liquid | 179.7 b |
| TJ 0300 | NK3030 | 0/100 | 5 | Brookings, SD | Liquid | 170.7ab |
| TJ 1300 | NK3030 | 50/50 | 2 | Brookings, SD | Liquid | 177.9 b |
| TJ 1310 | NK3030 | 30/70 | 4 | Brookings, SD | Liquid | 172.8ab |
| TJ 66/300 | NK3030 | 50/50 | 3 | Brookings, SD | Liquid | 175.0 b |
| CV % | | | | | | 7.38 |
| LSD (0.20%) | | | | | | 12.36 |

TABLE 6

Liquid Drench Treatment on Corn Variety NK2555 at Groton, SD Location

| Treatment | Variety | Ratio | Rank | Location | Trial | Yield |
|---|---|---|---|---|---|---|
| Control | NK2555 | 0/0 | 6 | Groton, SD | Liquid | 136.2 a |
| TJ 1000 | NK2555 | 100/0 | 1 | Groton, SD | Liquid | 147.7 c |
| TJ 0300 | NK2555 | 0/100 | 2 | Groton, SD | Liquid | 145.0bc |
| TJ 1300 | NK2555 | 50/50 | 3 | Groton, SD | Liquid | 142.5bc |
| TJ 1310 | NK2555 | 30/70 | 4 | Groton, SD | Liquid | 141.5abc |
| TJ 66/300 | NK2555 | 50/50 | 5 | Groton, SD | Liquid | 138.5abc |
| CV % | | | | | | 10.92 |
| LSD (0.20%) | | | | | | 8.42 |

TABLE 7

Liquid Drench Treatment on Corn Variety NK 3030Bt at Brookings, SD Location

| Treatment | Variety | Ratio | Rank | Location | Trial | Yield |
|---|---|---|---|---|---|---|
| Control | NK3030Bt | 0/0 | 4 | Brookings, SD | Liquid | 181.5 ab |
| TJ 1000 | NK3030Bt | 100/0 | 2 | Brookings, SD | Liquid | 185.5 b |
| TJ 0300 | NK3030Bt | 0/100 | 6 | Brookings, SD | Liquid | 171.3 a |
| TJ 1300 | NK3030Bt | 50/50 | 5 | Brookings, SD | Liquid | 180.7ab |
| TJ 1310 | NK3030Bt | 30/70 | 1 | Brookings, SD | Liquid | 185.8 b |
| TJ 66/300 | NK3030Bt | 50/50 | 3 | Brookings, SD | Liquid | 181.6 ab |
| CV % | | | | | | 6.32 |
| LSD (0.20%) | | | | | | 11.40 |

TABLE 8

Liquid Drench Treatment on Corn Variety 3030Bt at Groton, SD Location

| Treatment | Variety | Ratio | Rank | Location | Trial | Yield |
|---|---|---|---|---|---|---|
| Control | NK3030Bt | 0/0 | 2 | Groton, SD | Liquid | 173.9 c |
| TJ 1000 | NK3030Bt | 100/0 | 6 | Groton, SD | Liquid | 164.1 a |
| TJ 0300 | NK3030Bt | 0/100 | 4 | Groton, SD | Liquid | 171.3 abc |
| TJ 1300 | NK3030Bt | 50/50 | 3 | Groton, SD | Liquid | 171.5 abc |
| TJ 1310 | NK3030Bt | 30/70 | 1 | Groton, SD | Liquid | 176.3 c |
| TJ 66/300 | NK3030Bt | 50/50 | 5 | Groton, SD | Liquid | 164.4 ab |
| CV % | | | | | | 10.92 |
| LSD (0.20%) | | | | | | 8.42 |

Compatibility with Dry Granule Micro-Nutrient Fertilizer Working Example

Materials and Methods: A field trial was conducted using the corn variety NK 3030Bt at a location in Groton, S.Dak. The purpose of the trial was to compare the compatibility and yield benefit of the biocontrol preparation TJ1300 in combination with a dry granule micro-nutrient fertilizer vs. the micro-nutrient fertilizer alone vs. a control with no micro-nutrient fertilizer. The micro-nutrient fertilizer is sold commercially by the applicant under the trademark TJ Micromix™. Biocontrol treatments were prepared by adding $1 \times 10^6$ CFU per seed. The control seed was Maxim (Maxim is a trademark of Syngenta Crop Protection) treated with the biocontrol treatments applied in addition to the Maxim. The seed was planted at a seeding rate of 25,000 seeds per acre in 30-inch rows in a randomized, replicated block. TJ Micromix™ was applied at a rate of 20 pounds per acre. Each entry was replicated four times. The pathogen levels were natural populations at each location. The entries were as follows:

Control: Maxim
TJ Micromix
TJ Micromix+TJ 1300-50/50 combination of *B. amyloliquefaciens* TJ1000 or 1BE and
*T. virens* G1-3

Results: In this trial, as shown in Table 9, the Granular TJ Micromix produced a non-significant yield increase compared to the control. When the seed-applied biocontrol treatment TJ1300 was applied in combination with the TJ Micromix, the treatment resulted in a significant increase in yield.

Conclusion: The trial shows that TJ 1300 is compatible with micro-nutrient applications and the combination produces a significant yield response.

TABLE 9

Effect of TJ Micromix and TJ Micromix + TJ
1300 on Corn Variety NK 3030Bt

| Treatment | Variety | Rank | Location | Trial | Yield |
|---|---|---|---|---|---|
| Control | NK3030Bt | 3 | Groton, SD | Fertilizer | 157.0 a |
| TJ Micromix | NK3030Bt | 2 | Groton, SD | Fertilizer | 163.3 ab |
| TJ Micromix + TJ 1300 | NK3030Bt | 1 | Groton, SD | Fertilizer | 175.5 b |
| CV % | | | | | 9.04 |
| LSD (0.05%) | | | | | 5.64 |

Compatibility with Liquid Chelate Micro-Nutrient Fertilizer Working Example

Materials and Methods: A field trial was conducted using the corn variety NK 3030Bt at a location in Groton, S.Dak. The purpose of the trial was to compare the compatibility and yield benefit of the biocontrol preparation TJ1300 in combination with a liquid chelate micro-nutrient fertilizer vs. the liquid chelate micro-nutrient fertilizer alone. The liquid chelate micro-nutrient fertilizer is sold commercially under the Trademark TJ Micromix™-Cornmix. Biocontrol treatments were prepared by adding $1\times10^6$ CFU per seed. The control seed was Maxim (Maxim is a trademark of Syngenta Crop Protection) treated with the biocontrol treatments applied in addition to the Maxim. The seed was planted at a seeding rate of 25,000 seeds per acre in 30-inch rows in a randomized, replicated block. TJ Micromix™-Cornmix was applied at a rate of 1.5 quarts per acre. Each entry was replicated four times. The pathogen levels were natural populations at the location. The entries were as follows:

Control: Maxim+Liquid Chelate TJ Micromix

TJ Micro+TJ1000: Liquid Chelate TJ Micromix plus TJ 1000–*B. amyloliquefaciens* TJ1000 or 1BE TJ Micro+TJ0300: Liquid Chelate TJ Micromix plus TJ 0300–*T. virens* G1-3

TJ Micro+TJ1300: Liquid Chelate TJ Micromix+TJ 1300–50/50 combination of *B. amyloliquefaciens* TJ1000 or 1BE and *T. virens* G1-3

TJ Micro+TJ 1310: Liquid Chelate TJ Micromix+TJ 1310–Coculture 30/70 combination of *B. amyloliquefaciens* TJ1000 or 1BE and *T. virens* G1-3

TJ Micro+TJ66/300: Liquid Chelate TJ Micromix+TJ 66/300–50/50 combination of *Bacillus lentimorbus* and *T. virens* G1-3

Results: As shown in Table 10, the biocontrol treatments TJ1000, 66/300, and 1300 combined with the liquid chelate TJ Micromix resulted in a significant increase in yield over the control of TJ Micromix alone. The other biocontrol entries showed numerical but non-significant increases in yield. The conclusion was that the biocontrol agents used in this study are compatible with liquid chelate micro-nutrient applications. This biocontrol/liquid chelate micro-nutrient fertilizer combination is a viable means to significantly increase the yield of corn.

TABLE 10

Effect of TJ Micromix Liquid Chelate and TJ Micromix Liquid
Chelate + TJ 1300 on Yield of Corn Variety NK3030Bt

| Treatment | Variety | Ratio | Rank | Location | Trial | Yield |
|---|---|---|---|---|---|---|
| Control | NK3030Bt | 0/0 | 6 | Groton, SD | Liquid TJ Micromix | 161.0 a |
| TJ Micro + TJ 1000 | NK3030Bt | 100/0 | 3 | Groton, SD | Liquid TJ Micromix | 173.0 bc |
| TJ Micro + TJ 0300 | NK3030Bt | 0/100 | 5 | Groton, SD | Liquid TJ Micromix | 163.0 ab |
| TJ Micro + TJ 1300 | NK3030Bt | 50/50 | 1 | Groton, SD | Liquid TJ Micromix | 183.7 c |
| TJ Micro + TJ 1310 | NK3030Bt | 30/70 | 4 | Groton, SD | Liquid TJ Micromix | 172.0 ab |
| TJ Micro + TJ 66/300 | NK3030Bt | 50/50 | 2 | Groton, SD | Liquid TJ Micromix | 173.2 bc |
| CV % | | | | | | 11.2 |
| LSD (0.05%) | | | | | | 12.36 |

Sunflower Dry Granule Micro-Nutrient Fertilizer Working Example

Materials and Methods: A field trial was conducted using the sunflower variety Pioneer 63M80 NuSun at a location in Hazelton, N.Dak. The purpose of the trial was to compare the compatibility and yield benefit of the biocontrol preparation TJ1300 in combination with a dry granule micro-nutrient fertilizer vs. the micro-nutrient fertilizer alone vs. a control with no micro-nutrient fertilizer. Analyzing yield of sunflower is a function of seed yield in pounds per acre and the amount of oil in the seed which is expressed as a percentage. The micro-nutrient fertilizer is sold commercially under the Trademark TJ Micromix™. Biocontrol treatments were prepared by adding $1\times10^6$ CFU per seed. The control seed was Maxim (Maxim is a trademark of Syngenta Crop Protection) treated with the biocontrol treatments applied in addition to the Maxim. The seed was planted at a seeding rate of 22,000 seeds per acre in 30-inch rows in a randomized, replicated block. TJ Micromix™ was applied at a rate of 20 pounds per acre. Each entry was replicated four times. The pathogen levels were natural populations at the location. The entries were as follows:

Control: Maxim

TJ Micromix

TJ 1300—50/50 combination of *B. amyloliquefaciens* TJ1000 or 1BE and *T. virens* G1-3

TJ Micromix+TJ 1300-50/50 combination of *B. amyloliquefaciens* TJ1000 or 1BE and *T. virens* G1-3

Results: As shown in Table 11, in this trial, the Granular TJ Micromix produced a significant yield increase and a significant oil percentage increase compared to the control. When the seed-applied biocontrol treatment TJ1300 was applied in combination with the TJ Micromix, the treatment resulted in a significant increase in yield as compared to the control but not significantly different from the TJ Micromix application alone. The yield of the TJ 1300+TJ Micromix was numerically higher in yield. The conclusion was that TJ 1300 is compatible with micro-nutrient applications and may be a viable tool to increase the yield of sunflower.

TABLE 11

Effect of TJ 1300 Liquid Biological Treatment Plus Dry Granular TJ Micromix on Yield of Nu-sun Sunflower Variety 63M80

| Treatment | Rank | Location | Trial | Yield | Oil |
|---|---|---|---|---|---|
| Control | | Hazelton, ND | TJ Micro | 1709.7 a | 44.8 a |
| TJ Micromix | | Hazelton, ND | TJ Micro | 1857.3 bc | 47.2 b |
| TJ 1300 | | Hazelton, ND | TJ Micro | 1734.7ab | 45.5 a |
| TJ 1300 + TJ Micromix | | Hazelton, ND | MM | 1864.7 bc | 44.9 a |
| CV % | | | | 7.48 | 4.67 |
| LSD (0.20) | | | | 132.8 | 1.5 |

Sunflower Liquid Chelate Micro-Nutrient Working Example

Materials and Methods: Field trial was conducted using the sunflower variety Pioneer 63M80 NuSun at 3 locations: Hazelton, N.Dak.; Kensal, N.Dak.; and Selby, S.Dak. The purpose of each trial was to compare the compatibility and yield benefit of the biocontrol preparation TJ1300 in combination with a liquid chelate micro-nutrient fertilizer vs. an untreated control. Analyzing yield of sunflower is a function of seed yield in pounds per acre and the amount of oil in the seed which is expressed as a percentage. The liquid chelate micro-nutrient fertilizer is sold commercially under the Trademark TJ Micromix™. Biocontrol treatments were prepared by adding $1\times10^8$ CFU per gram to a wettable powder (Mycotech, Inc). 25 grams of the wettable powder was then added to 1.5 quarts of liquid chelate TJ Micromix and the combination applied in the seed furrow at a rate of 1.5 quarts per acre. The control seed was Maxim (Maxim is a trademark of Syngenta Crop Protection) treated with the biocontrol treatments applied in addition to the Maxim. The seed was planted at a seeding rate of 22,000 seeds per acre in 30-inch rows in a randomized, replicated block. Each entry was replicated four times. The pathogen levels were natural populations at each location. The entries were as follows:

Control—no treatment
TJ 1300-50/50 combination of *B. amyloliquefaciens* G1-3 and *T. virens* G1-3
TJ1300+TJ Micromix–Liquid chelate TJ Micromix+50/50 combination of *B. amyloliquefaciens* and *T. virens*

Result: As shown in Table 12, TJ Micromix liquid and the combination of TJ Micromix plus TJ 1300 both gave sunflower a significant increase in yield. TJ 1300+TJ Micromix produced an additional numerical increase in yield over the TJ Micromix alone.

Conclusion: TJ 1300+TJ Micromix is a viable means of biocontrol delivery on sunflower and is a viable means of increasing the seed yield of sunflower.

TABLE 12

Effect of TJ 1300 Biological Liquid Plus Liquid TJ Micromix Fertilizer on Yield of Nu-sun Sunflower Variety 63M80

| Treatment | Ratio | Location | Trial | Yield | Oil |
|---|---|---|---|---|---|
| Control | 0/0 | Hazelton, ND | Liquid TJ Micro | 1709.7 | 44.8 |
| TJ 1300 | 50/50 | Hazelton, ND | Liquid TJ Micro | 1765.0 | 45.5 |
| TJ 1300 + TJ Micromix | 50/50 | Hazelton, ND | Liquid TJ Micro | 1992.3 | 45.9 |
| Control | 0/0 | Kensal, ND | Liquid TJ Micro | 2000.3 | N/a |
| TJ 1300 | 50/50 | Kensal, ND | Liquid TJ Micro | 2159.0 | N/a |
| TJ 1300 + TJ Micromix | 50/50 | Kensal, ND | Liquid TJ Micro | 2329.0 | N/a |
| Control | 0/0 | Selby, SD | Liquid TJ Micro | 2225.0 | 43.2 |
| TJ 1300 | 50/50 | Selby, SD | Liquid TJ Micro | 2324.0 | 44 |
| TJ 1300 + TJ Micromix | 50/50 | Selby, SD | Liquid TJ Micro | 2228.5 | 44 |
| Control Average | | | | 1978.3 a | 44 a |
| TJ 1300 | | | | 2082.8 b | 44.75 a |
| TJ 1300 + TJ Micromix | | | | 2173.3 b | 45.5 a |
| CV % | | | | 10.58 | 4.67 |
| LSD (0.05) | | | | 104.1 | NS |

Soybean Liquid Chelate Micro-Nutrient Fertilizer Working Example

Materials and Methods: A field trial was conducted using the soybean variety Pioneer 91B52 a location near Groton, S.Dak. The purpose of the trial was to compare the compatibility and yield benefit of the biocontrol preparation TJ1300 in combination with a liquid chelate micro-nutrient fertilizer vs. the liquid chelate alone vs. an untreated control. Yield in bushels per acre was used as the measure of the treatment response. The liquid chelate micro-nutrient fertilizer is sold commercially under the Trademark TJ Micromix™. Biocontrol treatments were prepared by adding $1\times10^8$ CFU per gram to a wettable powder (Mycotech, Inc). Twenty-five grams of the wettable powder was then added to 10 gallons of water and applied in the seed furrow at a rate of 10 gallons per acre to establish treatment TJ1300. Twenty-five grams of the wettable powder was added to 1.5 quarts of liquid chelate TJ Micromix and the combination added to water to form a 10 gallon solution and applied in the seed furrow at a rate of 10 gallons per acre. The seed was planted at a seeding rate of 175,000 seeds per acre in 30-inch rows in a randomized, replicated block. Each entry was replicated four times. The pathogen levels were natural populations at the location. The entries were as follows:

Control—no treatment
TJ 1300–50/50 combination of *B. amyloliquefaciens* TJ1000 or 1BE and *T. virens* G1-3
TJ1300+TJ Micromix–Liquid chelate TJ Micromix+50/50 combination of *B. amyloliquefaciens* TJ1000 or 1BE and *T. virens* G1-3

Result: As shown in Table 13, TJ Micromix liquid and the combination of TJ Micromix plus TJ 1300 both gave soybean a significant increase in yield. TJ 1300+TJ Micromix produced an additional numerical but non significant increase in yield over the TJ Micromix alone.

Conclusion: TJ 1300+TJ Micromix is a viable means of biocontrol deliver on soybean and is a viable means of increasing the yield of soybean.

TABLE 13

Effect of TJ 1300 Liquid Biological Treatment Plus Liquid
TJ Micromix Fertilizer on Yield of Soybean Variety 91B52

| Treatment | Ratio | Location | Trial | Yield |
|---|---|---|---|---|
| Control | 0/0 | Groton, SD | Liquid TJ Micromix | 54.2 a |
| TJ 1300 | 50/50 | Groton, SD | Liquid TJ Micromix | 60.8 b |
| TJ 1300 + TJ Micromix | 50/50 | Groton, SD | Liquid TJ Micromix | 61.8 b |
| CV % | | | | 8.92 |
| LSD (0.05) | | | | 4.19 |

Soybean Dry Granule Micro-Nutrient Working Example

Materials and Methods: A field trial was conducted using the soybean variety Pioneer 91B52 at a location near Groton, S.Dak. The purpose of the trial was to compare the compatibility and yield benefit of the biocontrol preparation TJ1300 in combination with a dry granule micro-nutrient fertilizer vs. the micro-nutrient fertilizer alone vs. a control with no micro-nutrient fertilizer. Soybean yield in bushels per acre was used to measure the treatment response. The micro-nutrient fertilizer is sold commercially under the Trademark TJ Micromix™. Biocontrol treatments were prepared by adding $1 \times 10^5$ CFU per seed. The seed was planted at a seeding rate of 175,000 seeds per acre in 30-inch rows in a randomized, replicated block. TJ Micromix™ was applied at a rate of 20 pounds per acre. Each entry was replicated four times. The pathogen levels were natural populations at each location. The entries were as follows:

Control: Maxim

TJ Micromix

TJ 1300–50/50 combination of *B. amyloliquefaciens* TJ1000 or 1BE and *T. virens* G1-3

TJ Micromix+TJ 1300-50/50 combination of *B. amyloliquefaciens* TJ1000 or 1BE and *T. virens* G1-3

Results: As shown in Table 14, in this trial, the Granular TJ Micromix produced a significant yield increase compared to the control. When the seed-applied biocontrol treatment TJ1300 was applied in combination with the TJ Micromix, the treatment resulted in a significant increase in yield as compared to the control but not significantly different from the TJ Micromix application alone. The yield of the TJ 1300+ TJ Micromix was numerically higher.

Conclusion: TJ 1300 is compatible with micro-nutrient applications and is a viable tool to increase the yield of soybean.

TABLE 14

Effect of TJ 1300 Biological Seed Treatment Plus Dry Granule
TJ Micromix Fertilizer on Yield of Soybean Variety 91B52

| Treatment | Ratio | Location | Trial | Yield |
|---|---|---|---|---|
| Control | 0/0 | Groton, SD | TJ Micro | 54.2 a |
| TJ Micromix Granule | 0/0 | Groton, SD | TJ Micro | 61.6 b |
| TJ 1300 | 50/50 | Groton, SD | TJ Micro | 62.5 b |
| TJ 1300 + TJ Micromix | 50/50 | Groton, SD | TJ Micro | 63.3 b |
| CV % | | | | 8.92 |
| LSD (0.05) | | | | 4.19 |

Spring Wheat Working Example

Materials and Methods: A field trial was conducted using Russ Spring wheat at a location near Kensal, N.Dak. The purpose of the trial was to test biocontrol TJ 1300 on spring wheat against an untreated control. The biocontrol TJ 1300 was applied to the seed so as to achieve an application rate of $2.5 \times 10^9$ CFU per acre. The plot was planted in a randomized, replicated block design with each entry replicated three times.

Result: As shown in Table 15, the entry TJ 1300 produced a non-significant yield increase. The conclusion was that TJ 1300 may be of value as a seed treatment on wheat.

TABLE 15

Effect of TJ 1300 Biological Seed Treatment
Plus Fertilizer on Russ Spring Wheat

| Treatment | Ratio | Location | Trial | Yield |
|---|---|---|---|---|
| Control | 0/0 | Kensal, ND | MM | 43.8 |
| 1300 | 50/50 | Kensal, ND | MM | 44.0 |
| CV % | | | | 7.52 |
| LSD (0.05) | | | | NS |

Field Peas Working Example

Materials and Methods: A field trial was conducted to compare the biocontrol treatment TJ 1300 to a non-treated control on field peas. The seed was treated with the biocontrol agent to achieve an application of $2.5 \times 10^9$ CFU per acre. Yield response was measured as pounds per acre.

Results: As shown in Table 16, the entry TJ 1300 produced a non-significant yield increase in field peas. The conclusion was that TJ 1300 may be an effective tool to increase the yield of field peas.

TABLE 16

Effect of TJ 1300 Biological Seed Treatment
on Yield of Integra Field Pea

| Treatment | Ratio | Rep | Location | Trial | Yield | Test weight |
|---|---|---|---|---|---|---|
| Control | 0/0 | Ave of 3 | Carrington, ND | Pea | 3590.0 | 62.9 |
| 1300 | 50/50 | Ave of 3 | Carrington, ND | Pea | 3613.0 | 63.5 |
| CV % | | | | | 7 | 0.5 |
| LSD (0.05) | | | | | ns | Ns |

Increased Manganese Uptake Working Example

A surprising aspect of the subject invention is that plants that grow from seeds treated with the disclosed combination experience increased uptake of manganese. The protective nature of increased manganese uptake is documented in Project S-269: Biological Control and Management of Soil-borne Plant Pathogens for Sustainable Crop Production, 5th International Conference on the Biogeochemistry of Trace Elements. Jul. 11-15 1999. Vienna, Austria, p. 1086-1087. Dr. Don Huber of Purdue University has documented the connection between an imbalance in the ratio of nitrogen to manganese and the incidence of stalk rot in corn. (Huber D.

2000. "Hidden Hunger" threatens many crops. Purdue News. Online at WWW URL purdue.edu/UNS/html4ever/ 0012.Huber.deficiency.html or news.uns.purdue.edu/UNS/ html4ever/0012.Huber.deficiency.html The disclosed combination of *Trichoderma virens* and *Bacillus amyloliquefaciens* for the purpose of plant pathogen control and increased plant yield thus has unexpected characteristics. The first is the fact that the combination produces an increase in yield, not just plant protection from the pathogen. Plant tissue analysis from test plots presented in Tables 17 and 18 below show an unexpected trend toward higher nutrient intake of a nutrient, manganese.

The treatments that produced the surprising results shown in Table 17 are defined as follows:

bs-unt-bt=Brookings, SD location–no treatment on the seed–Bt variety of corn ax-bt=Brookings, SD location–chemical fungicide Maxim on the seed–Bt variety of corn bs-1000-bt=Brookings, SD location–*Bacillus amyloliquefaciens* TJ 1000 on the seed–Bt variety bs-0300-bt=Brookings, SD location–*Trichoderma virens* G1-3 on the seed–Bt variety of corn bs-1300-bt=Brookings, SD location–*B. amyloliquefaciens* TJ 1000 and *T. virens* G1-3 (1 to 1 ratio) on the seed–Bt variety of corn bs-1310-bt=Brookings, SD location–*B. amyloliquefaciens* TJ 1000 and *T. virens* G 1-3 (7 to 3 ratio) on the seed–Bt variety of corn bs-66/300-bt=Brookings, SD location–*B. lentimorbus* and *T. virens* G1-3 (1 to 1 ratio) on the seed–Bt variety of corn The term "Bt" is defined as: A corn hybrid that has been genetically modified by the insertion of a gene from the bacteria *Bacillus thuringiensis*. The inserted gene produces a protein that will kill European corn bore that feed on the plant tissue.

bl-max-non=Brookings location–chemical fungicide Maxim on the seed–non Bt variety of corn bl-1000-non=Brookings location–*Bacillus amyloliquefaciens* TJ 1000 on the seed–non Bt variety of corn bl-300-non=Brookings location–*Trichoderma virens* G1-3 on the seed–non Bt variety of corn bl-1300-non=Brookings location–*B. amyloliquefaciens* TJ 1000 and *T. virens* G1-3 on the seed (1 to 1 ratio)–non Bt variety of corn (one of the claimed combinations)

bl-1310-non=Brookings location–*B. amyloliquefaciens* TJ 1000 and *T. virens* G1-3 on the seed (7 to 3 ratio)—non Bt variety of corn bl-66/300-non=Brookings location–*B. lentimorbus* and *T. virens* G1-3 on the seed (1 to 1 ratio)–non Bt variety of corn

TABLE 17

Effects of Treatments on Plant Mineral Content on Bt Variety of Corn at Brookings SD Location

| Treatment | Concentration | | | | | | | | | | | |
|---|---|---|---|---|---|---|---|---|---|---|---|---|
| | N | P | K | Mg | Ca | S | Na | Fe | Mn | B | Cu | Zn |
| bs-unt-bt | 3.43 | 0.39 | 1.65 | 0.66 | 1.11 | 0.29 | 0.003 | 110 | 105 | 17 | 18 | 32 |
| bs-max-bt | 3.42 | 0.43 | 2.10 | 0.56 | 0.91 | 0.27 | 0.005 | 117 | 91 | 14 | 18 | 29 |
| bs-1000-bt | 3.44 | 0.40 | 2.10 | 0.52 | 0.86 | 0.24 | 0.004 | 96 | 91 | 12 | 13 | 25 |
| bs-300-bt | 3.38 | 0.41 | 2.02 | 0.58 | 1.00 | 0.27 | 0.004 | 97 | 98 | 12 | 14 | 25 |
| bs-1300-bt | 3.36 | 0.43 | 1.89 | 0.66 | 1.11 | 0.27 | 0.004 | 118 | 134 | 13 | 16 | 28 |
| bs-1310-bt | 3.45 | 0.41 | 1.69 | 0.59 | 1.02 | 0.25 | 0.004 | 182 | 106 | 16 | 15 | 27 |
| bs-66/300-bt | 3.30 | 0.42 | 2.19 | 0.58 | 1.04 | 0.27 | 0.004 | 112 | 107 | 16 | 15 | 29 |

TABLE 18

Effects of Treatments on Plant Mineral Content on Non Bt Variety of Corn at Brookings SD Location

| Treatment | Concentration | | | | | | | | | | | |
|---|---|---|---|---|---|---|---|---|---|---|---|---|
| | N | P | K | Mg | Ca | S | Na | Fe | Mn | B | Cu | Zn |
| bl-unt-non | 3.33 | 0.39 | 1.93 | 0.55 | 0.85 | 0.21 | 0.005 | 76 | 103 | 12 | 13 | 24 |
| bl-max-non | 3.28 | 0.48 | 2.39 | 0.62 | 0.92 | 0.24 | 0.007 | 101 | 116 | 12 | 15 | 28 |
| bl-1000-non | 3.14 | 0.51 | 2.39 | 0.64 | 0.95 | 0.25 | 0.008 | 103 | 115 | 12 | 15 | 26 |
| bl-300-non | 3.19 | 0.48 | 2.21 | 0.65 | 0.93 | 0.24 | 0.009 | 95 | 99 | 15 | 15 | 24 |
| bl-1300-non | 3.38 | 0.48 | 2.43 | 0.60 | 0.96 | 0.25 | 0.006 | 111 | 137 | 13 | 15 | 26 |
| bl-1310-non | 3.21 | 0.46 | 2.18 | 0.68 | 1.03 | 0.26 | 0.007 | 108 | 117 | 18 | 16 | 25 |
| bl-66/300-non | 3.23 | 0.43 | 1.96 | 0.61 | 0.86 | 0.23 | 0.009 | 93 | 95 | 11 | 13 | 25 |

The treatments that produced the surprising results in Table 18 are defined as follows:

bl-unt-non=Brookings location–no treatment on the seed–non Bt variety of corn (non Bt can also be described as: non genetically modified)

Manganese is known in the art as a disease prevention micronutrient. However, if manganese is added to fertilizer and applied to corn, the expected result is a decrease in yield. The significance of the subject invention is that it increases the manganese content of the corn plant while increasing yield. Furthermore, the increase in the manganese content in the plant does not occur with either organism alone or when the *Trichoderma virens* is combined with a different organism (e.g., treatment 66/300) or the formulation of the mixture is altered (e.g., treatment 1310). This increase in manganese content of the plant tissue is documented in tables 1 and 2 above on Bt (genetically modified) corn and conventional (non-genetically modified) corn. Tissue analysis of the corn in the charts above was done after the silking and pollination of the corn, documenting that this increase in manganese continues into the late stages of growth. Late season intake is significant because the lack of manganese in the plant is implicated in mid to late season stalk rot.

Data from disclosed combinations of the *Trichoderma* with other bacteria strains show that other combinations tested did not increase the manganese levels to the level of the present invention. It is surprising that neither organism alone increased the manganese level in the tissue of the corn. Only seed treatment with the claimed combination of the *T. virens* G1-3 fungus and the *B. amyloliquefaciens* bacterium increase the manganese level in the tissue of both the Bt and non-Bt corn.

Consistency of Increased Yield Working Example

Another surprising aspect of the subject invention is unexpected consistency of increased yield: (1) consistency compared to either organism alone, in that our field trial results show the claimed combination to be significantly higher in yield over the control in both individual locations and multiple location and either organism alone did not produce a significant yield response over the control; (2) consistency across geography, in that the field trial results show the combination to be effective in a number of geographies from North Dakota to Arizona; and (3) consistency of higher yield in a more than one crop, in that the field data collected on corn, soybeans, sunflowers and wheat show significant increased in yield with the claimed combination. Field trial results are presented in the above working examples. The results of those field trials produced a surprisingly consistent yield response, and consistency is what is commercially important.

The disclosed combination of microorganisms gives more consistent yield response than either microorganism alone. The claimed combination produces a consistent increase in yield over a range of conditions while alone the microorganisms do not. The data in the patent application show this, but the data presented in Table 19 below that was produced at the experiment station in Carrington, N.Dak. show this effect.

TABLE 19

Consistency of Yield Response

|  | 2000 | 2001 | 2002 | 3 YR |
|---|---|---|---|---|
| Control | 96.9 | 146 | 87.7 | 110.2 |
| Bacillus | 93.3 | 150 | 94.9 | 112.7 |
| T. virens | 94.7 | 162 | 88.5 | 115.1 |
| QuickRoot | 105.6 | 156 | 90.4 | 117.3 |
| 1310 | 89.5 | 151 | 88.5 | 109.6 |

In Table 19, the treatments are defined as follows:
Control=chemical fungicide Maxim
Bacillus=*B. amyloliquefaciens* alone
*T. virens*=*T. virens* G1-3 alone
Quick Root=QuickRoots™ is the product name of the claimed combination of *T. virens* G1-3 and *B. amyloliquefaciens*
1310=*T. virens* G1-3 and *B. amyloliquefaciens* at a 7:3 ratio.

The column headings in Table 19 denote the year of the trial with "3YR" indicating the average treatment response for the combined three years. Note that in 2000, seed treatment with the individual organisms alone (the individual components of the claimed combination) produced yields that were less than control. In 2001, seed treatment with individual organisms both produced yields that were greater than the control as did the claimed combination. In 2002, seed treatment with the individual organisms produced yields that were greater than the control and again the claimed combination increased yield as well.

The North Dakota data presented in Table 19 document consistency in two of ways. First, in reviewing year 2000 data, neither the *Bacillus* bacteria (1000) seed treatment nor the *Trichoderma* fungi (G1-3) seed treatment by themselves produced a positive yield response; but the claimed combination did produce a positive response. Two negative responses added together do not produce a positive. Synergism is what creates positive response from two negatives. In years 2001 and 2002, the performance of treatments with the bacteria and the fungi traded places as the top seat while the performance of the claimed combination performed between treatments with the individual components. Overall, the consistent performance of the claimed combination gave the largest yield advantage because of consistency of response. These data are from the same location; only weather changed from season to season. The *Bacillus* alone seed treatment did not perform well at all in the average and the *Trichoderma* alone seed treatment only averaged well because it had one great performance out of three.

Presented in Table 20 is a compilation of data from three years of field trials, 63 entries, at 12 locations. The test plots were located at North Dakota State University, University of Arizona, and Colorado State University. This compilation clearly shows the 50/50 combination of *B. amyloliquefaciens*+*T. virens* (one of the claimed combinations) produces a significantly higher yield than the control and than either organism alone. It should be noted that while the individual components show a numerical increase in yield, it is a non-significant increase at a 0.05 rejection level while the claimed combination is significant at a 0.05 rejection level.

TABLE 20

QuickRoots ™ Effect on Corn Yield in Replicated Field Trials.
3 Year Average Evaluating QuickRoots ™/Maxim vs. Maxim

| Treatment | Moisture | Yield | Pricing | Advantage |
|---|---|---|---|---|
| Control | 17.5 | 154.77 | $300.25 |  |
| B. amyloliquefaciens alone | 17.5 | 158.7 | $307.88 | $ 7.62 |
| T. virens alone | 17.4 | 158.81 | $308.57 | $ 8.31 |
| B. amyloliquefaciens + T. virens combined 50/50 | 17.5 | 161.62 | $313.54 | $13.29 |
| Mean | 17.5 | 158.88 | $307.56 |  |
| CV (%) | 23.3 | 21.7 |  |  |
| LSD (0.05) | .19(NS) | 5.05 |  |  |

Corn Variety NK 2555 Treatment with Other Strains Working Example

Materials and Methods: For these studies *Trichoderma virens* G1-21 (an isolate that is commercially available from Thermo Trilogy Corporation) and *Bacillus subtilis* var. *amyloliquefaciens* FZB24 (a strain that is commercially available from Earth Biosciences, Inc.) were selected. The plot entries (treatments) were as follows:

Treatment A—Control (MAXIM, industry standard fungicide seed treatment)

Treatment B—*T. virens* G1-3+*Bacillus subtilis* var. *amyloliquefaciens* TJ 1000

Treatment C—*T. virens* G1-21+*Bacillus subtilis* var. *amyloliquefaciens* TJ 1000

Treatment D—*T. virens* G1-3+*Bacillus subtilis* var. *amyloliquefaciens* FZB24

Treatment E—*T. virens* G1-21+*Bacillus subtilis* var. *amyloliquefaciens* FZB24

The treatments were applied to corn seed (NK 2555) at equal rates of at least $1 \times 10^6$ fungal spores and $1 \times 10^6$ bacterial spores per seed. Previous field trials had confirmed that Treatment B produced an unexpected synergism that consistently and significantly increased yield in plants. The follow up field trials were conducted with the same test protocol as the initial trials and set up as a randomized—replicated block.

Results: Presented in Table 21 are the results of this trial. In this trial, all of the *T. virens*–*Bacillus subtilis* var. *amyloliquefaciens* combinations produced a numerically positive response. These results gave strong indication that combinations of *T. virens* and *Bacillus subtilis* var. *amyloliquefaciens* produce a synergistic effect that is similar to that discovered when *Trichoderma virens* G1-3 and *Bacillus subtilis* var. *amyloliquefaciens* TJ 1000 were combined and placed in the vicinity of the seed.

TABLE 21

Treatment of Corn Variety NK 2555 with Other Strains and Isolates

| Treatment | Test Weight | Moisture | Yield |
|---|---|---|---|
| A | 55.9 | 21.8 | 173.6 |
| B | 56.9 | 20.4 | 177.2 |
| C | 56.9 | 20.3 | 183.2 |
| D | 56.3 | 20.9 | 181.1 |
| E | 55.7 | 20.6 | 182.2 |
| C.V. | 5.4 | | |
| LSD .05 | 16.3 | | |

Corn Variety NK 3030 Bt Treatment with Other Strains Working Example

This trial compared the treatment of *Trichoderma virens* G1-3 and *Bacillus subtilis* var. *amyloliquefaciens* TJ 1000 vs. *Trichoderma virens* GL-21 and *Bacillus subtilis* var. *amyloliquefaciens* FZB24 vs. a control (Maxim, industry standard fungicide seed treatment). Plot entries were as follows:

Treatment A—Control (MAXIM, industry standard fungicide seed treatment)

Treatment B—*T. virens* G1-3 and *Bacillus subtilis* var. *amyloliquefaciens* TJ 1000

Treatment C—*T. virens* G1-21 and *Bacillus subtilis* var. *amyloliquefaciens* FZB24

Materials and Methods: Corn seed (NK 3030 Bt) was treated at the same rate of *Bacillus* and *Trichoderma* as in the previous working example and the seed was planted in a randomized—replicated block design.

Results: Presented in Table 22 are the results of this trial. In this trial, the yields of Treatments B and C were significantly greater than the control. Treatment B was numerically superior to Treatment C but not significantly. The results of this trial also indicated that other combinations of *T. virens* and *Bacillus subtilis* var. *amyloliquefaciens* can be expected to show a synergistic response.

TABLE 22

Treatment of Corn Variety NK 3030 Bt with Other Strains and Isolates

| Treatment | Test Weight | Moisture | Yield |
|---|---|---|---|
| A | 52.5 | 21.5 | 172.1 |
| B | 54.6 | 21.5 | 210.0 |
| C | 55.3 | 21.6 | 192.8 |
| C.V. | 8.09 | | |
| LSD .05 | 19.43 | | |

Combined Trials with Other Strains Working Example

This example compared the same treatments as the previous working example, which were as follows: *Trichoderma virens* G1-3 and *Bacillus subtilis* var. *amyloliquefaciens* TJ 1000 vs. *Trichoderma virens* G1-21 and *Bacillus subtilis* var. *amyloliquefaciens* FZB24 vs. a control (MAXIM). This trial differed from the previous working example because it compared 43 entries from 12 locations and 6 different corn hybrids. Plot entries were as follows:

Treatment A—Control (MAXIM, industry standard fungicide seed treatment)

Treatment B—*T. virens* G1-3 and *Bacillus subtilis* var. *amyloliquefaciens* TJ 1000

Treatment C—*T. virens* G1-21 and *Bacillus subtilis* var. *amyloliquefaciens* FZB24

Materials and Methods: Seed was treated the same as in the previous two trials and each location was randomized and replicated.

Results: Presented in Table 23 are the results of this trial. This trial used a larger data set and revealed that the yield increase with the originally discovered combination of Treatment B (*Trichoderma virens* G1-3 and *Bacillus subtilis* var. *amyloliquefaciens* TJ 1000) is significantly greater than the control while the yield increase with Treatment C (*T. virens* G1-21 and *Bacillus subtilis* var. *amyloliquefaciens* FZB24) is not significantly greater, even at the 0.20 rejection level. However, Treatment C did not show a numerical yield decrease nor did it show a significant yield decrease compared to the control. A yield decrease compared to the control would most likely have occurred if the microorganisms in the combination were antagonistic to each other. This result clearly showed that the original discovery (Treatment B) was superior to the Treatment C. The result also showed that Treatment C is a potentially beneficial treatment.

TABLE 23

Treatment with Other Strains and Isolates

| Treatment | Yield in Bushels per Acre |
|---|---|
| A | 153.84 |
| B | 160.63 |
| C | 156.36 |
| C.V. | 3.42 |
| LSD .20 | 4.4 |

Many variations of the invention will occur to those skilled in the art. Some variations include non-competitive culturing of the biocontrol organisms. Other variations call for competitive culturing. All such variations are intended to be within the scope and spirit of the invention.

What is claimed is:

1. An agricultural inoculum suitable for inoculating plant seeds, said inoculum comprising:
a *Trichoderma virens* fungal antagonist selected from the group consisting of strain ATCC 58678 and strain G1-21;
a *Bacillus subtilis* var. *amyloliquefaciens* bacterial antagonist selected from the group consisting of strain ATCC BAA-390 and strain FZB24; and
a suitable carrier that is non-phytotoxic, non-bacteriostatic, and non-bactericidal.

2. A composition of matter made by combining:
a composition made by combining a plurality of antagonists selected from the group consisting of
a *Trichoderma virens* antagonist comprising strain G1-21 and a *Bacillus amyloliquefaciens* antagonist comprising strain FZB24;
a *Trichoderma virens* antagonist comprising strain ATCC 58678 and a *Bacillus amyloliquefaciens* antagonist comprising strain FZB24; and
a suitable carrier that is non-phytotoxic, non-bacteriostatic, and non-bactericidal.

3. An antagonist for controlling plant pathogens made by combining effective amounts of:
a fungal antagonist comprising *Trichoderma virens* strain G1-21;
a bacterial antagonist comprising *Bacillus amyloliquefaciens* strain FZB24; and
a suitable carrier that is non-phytotoxic, non-bacteriostatic, and non-bactericidal.

4. An antagonist made by further combining with the antagonist of claim 3 another bacterial strain.

5. An antagonist for controlling plant pathogens made by combining effective amounts of:
a fungal antagonist comprising a *Trichoderma virens* strain G1-21;
a plurality of bacterial antagonists; and
a suitable carrier that is non-phytotoxic, non-bacteriostatic, and non-bactericidal;
wherein the plurality of bacterial antagonists comprises a *Bacillus amyloliquefaciens* strain FZB24.

* * * * *